US010357490B2

(12) United States Patent
Hornby et al.

(10) Patent No.: US 10,357,490 B2
(45) Date of Patent: *Jul. 23, 2019

(54) COMBINATIONS FOR THE TREATMENT OF NEUROBLASTOMA

(71) Applicant: IGNYTA, INC., San Diego, CA (US)

(72) Inventors: Zachary Dolph Hornby, San Diego, CA (US); Gang Li, San Diego, CA (US); David Wesley Anderson, Poway, CA (US); Garrett M Brodeur, Wynnewood, PA (US); Radhika Iyer, Wilmington, DE (US)

(73) Assignee: IGNYTA, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/051,815

(22) Filed: Aug. 1, 2018

(65) Prior Publication Data

US 2019/0070173 A1    Mar. 7, 2019

Related U.S. Application Data

(63) Continuation of application No. 14/953,969, filed on Nov. 30, 2015, now Pat. No. 10,085,979.

(60) Provisional application No. 62/086,366, filed on Dec. 2, 2014.

(51) Int. Cl.
A61K 45/06 (2006.01)
A61K 31/495 (2006.01)
A61K 31/496 (2006.01)
C07D 231/56 (2006.01)
C07D 403/12 (2006.01)
C07D 405/12 (2006.01)
A61K 31/4188 (2006.01)
A61K 31/4745 (2006.01)

(52) U.S. Cl.
CPC ........ *A61K 31/496* (2013.01); *A61K 31/4188* (2013.01); *A61K 31/4745* (2013.01); *A61K 31/495* (2013.01); *A61K 45/06* (2013.01); *C07D 231/56* (2013.01); *C07D 403/12* (2013.01); *C07D 405/12* (2013.01)

(58) Field of Classification Search
CPC .............. A61K 31/496; A61K 31/4188; A61K 31/4745; A61K 45/06; A61K 31/495; C07D 403/12; C07D 231/56; C07D 405/12
See application file for complete search history.

(56) References Cited

U.S. PATENT DOCUMENTS

| 4,555,402 | A | 11/1985 | Matsuda et al. |
| 7,015,231 | B2 | 3/2006 | Lackey et al. |
| 7,230,098 | B2 | 6/2007 | Cui et al. |
| 7,534,792 | B2 | 5/2009 | Wittman et al. |
| 7,790,756 | B2 | 9/2010 | Flynn et al. |
| 7,799,782 | B2 | 9/2010 | Munson et al. |
| 7,964,592 | B2 | 6/2011 | Garcia-Echeverria et al. |
| 8,114,865 | B2 | 2/2012 | Bandiera et al. |
| 8,114,989 | B2 | 2/2012 | Wang et al. |
| 8,299,057 | B2 | 10/2012 | Lombardi Borgia et al. |
| 8,372,858 | B2 | 2/2013 | Michellys et al. |
| 8,404,846 | B2 | 3/2013 | Claridge et al. |
| 8,497,284 | B2 | 7/2013 | Bannen et al. |
| 8,513,263 | B2 | 8/2013 | Haas et al. |
| 8,673,893 | B2 | 3/2014 | Lombardi Borgia et al. |
| 8,680,111 | B2 | 3/2014 | Bailey et al. |
| 9,102,662 | B2 | 8/2015 | Lombardi Borgia et al. |
| 10,085,979 | B2 | 10/2018 | Hornby et al. |
| 10,231,965 | B2 | 3/2019 | Lim et al. |
| 2004/0014802 | A1 | 1/2004 | Dutruc-Rosset et al. |
| 2005/0014829 | A1 | 1/2005 | Remenar et al. |
| 2009/0263397 | A1 | 10/2009 | Buck et al. |
| 2010/0197665 | A1 | 8/2010 | Bandiera et al. |
| 2013/0018036 | A1 | 1/2013 | Lombardi Borgia et al. |
| 2014/0107107 | A1 | 4/2014 | Gautschi et al. |
| 2015/0051222 | A1 | 2/2015 | Barbugian et al. |
| 2015/0283132 | A1 | 10/2015 | Lim et al. |
| 2017/0007599 | A1 | 1/2017 | Lim et al. |
| 2017/0065582 | A1 | 3/2017 | Hornby et al. |
| 2018/0177792 | A1 | 6/2018 | Wei |
| 2018/0333412 | A1 | 11/2018 | Lim et al. |
| 2019/0000840 | A1 | 1/2019 | Li et al. |
| 2019/0022089 | A1 | 1/2019 | Codallos et al. |
| 2019/0070173 | A1 | 3/2019 | Hornby et al. |

FOREIGN PATENT DOCUMENTS

| CN | 101594862 | 12/2009 |
| CN | 101754956 | 6/2010 |
| CN | 102924479 A | 2/2013 |
| JP | 2002-275068 A | 9/2002 |
| WO | WO-99/43302 A1 | 9/1999 |
| WO | WO-03/051847 A1 | 6/2003 |
| WO | WO-03/078403 A2 | 9/2003 |
| WO | WO-2004/007676 | 1/2004 |

(Continued)

OTHER PUBLICATIONS

Adriaenssens, E. et al., Nerve growth factor is a potential therapeutic target in breast cancer, Cancer Res, Jan. 15, 2008, 68(2):346-351.
Albaugh, P. et al., Discovery of GNF-5837, a selective TRK inhibitor with efficacy in rodent cancer tumor models, Med. Chem. Lett, 2012, 3:140-145.
Alecensa® (alectinib) capsules, for oral use, Prescribing Information, Dec. 2015, 16 pp.
Asaumi, K. et al., Expression of neurotrophins and their receptors (TRK) during facture healing, Bone, Jun. 2000, 26(6);625-633.
Aveic et al., "Study of pan-Trk, ROS1, ALK inhibitor, RXDX-101, activity on human neuroblastoma cell lines", Brochure, SIOPEN Annual Meeting 2014, Apr. 23-25, 2014. (1 page).

(Continued)

Primary Examiner — Shirley V Gembeh
(74) Attorney, Agent, or Firm — Foley & Lardner LLP

(57) ABSTRACT

Disclosed are methods of treating neuroblastoma in a cancer patient by administration of a Trk inhibitor in combination with one more chemotherapeutic agents. Also disclosed are pharmaceutical compositions comprising a Trk inhibitor and one or more chemotherapeutic agents.

20 Claims, 3 Drawing Sheets

(56) References Cited

FOREIGN PATENT DOCUMENTS

| | | |
|---|---|---|
| WO | WO-2004/022544 A1 | 3/2004 |
| WO | WO-2004/062662 A1 | 7/2004 |
| WO | WO-2004/075898 A1 | 9/2004 |
| WO | WO-2005/040413 A1 | 5/2005 |
| WO | WO-2006/003276 A1 | 1/2006 |
| WO | WO-2006/080450 A1 | 8/2006 |
| WO | WO-2006/111035 A1 | 10/2006 |
| WO | WO-2007/017497 A2 | 2/2007 |
| WO | WO-2007/075847 A2 | 7/2007 |
| WO | WO-2008/003396 A1 | 1/2008 |
| WO | WO-2008/073480 A1 | 6/2008 |
| WO | WO-2008/074749 A1 | 6/2008 |
| WO | WO-2009/013126 A1 | 1/2009 |
| WO | WO-2013/119950 A2 | 8/2013 |
| WO | WO-2013/174876 A1 | 11/2013 |
| WO | WO-2014/093750 A1 | 6/2014 |
| WO | WO-2015/124697 A1 | 8/2015 |
| WO | WO-2015/189814 A1 | 12/2015 |
| WO | WO-2016/089760 A1 | 6/2016 |
| WO | WO-2016/089853 A1 | 6/2016 |
| WO | WO-2017/106492 A1 | 6/2017 |

OTHER PUBLICATIONS

Awad et al., "ALK inhibitors in non-small cell lung cancer: crizotinib and beyond", Clin Adv Hemotol Oncol, Jul. 2014, 12(7):429-439.
Bardelli, A. et al., Mutational analysis of the tyrosine kinome in colorectal cancers, Science, 2003, 300:949.
Bardelli, A. et al., Mutational analysis of the tyrosine kinome in colorectal cancers, Science, 2003, 300:949; Supplemental Material.
Baserga, R. et al., the IGF-I receptor in cell growth, transformation and apoptosis, Biochip Biophys Acta, 1997, 1332:F105-F126.
Bavetsias, V. et al., Hit generation and exploration: imidazo[4,5-b]pyridine derivatives as inhibitors of aurora kinases, Bioorganic & Medicinal Chemistry Letters, 2007, 17:6567-6571.
Bergethon, K. et al., ROS1 rearrangements define a unique molecular class of lung cancers, Journal of Clinical Oncology, Mar. 10, 2012, 30(8):863-870.
Bouhana, K. et al., LOXO-101, a pan TRK inhibitor, for the treatment of TRK-driven cancers, 26th EORTC-NCI-AACR Symposium on Molecular Targets and Cancer Therapeutics, Barcelona, Spain, Poster, Nov. 2014, Abstract #291, 1 p.
Brodeur, G. M., Neuroblastoma: biological insights into a clinical enigma, Nat. Rev. Cancer, Mar. 2003, 3:203-216.
Brodeur, Gm, et al. Trk receptor expression and inhibition in neuroblastomas. Clin Cancer Res. May 15, 2009;15(10):3244-50.
Broekman, F. et al., Tyrosine kinase inhibitors: multi-targeted or single-targeted?, World J. Clin Oncol, Feb. 10, 2011, 2(2):80-93.
Brose, M. et al., LOXO-101, a selective pan-TRK inhibitor for patients with TRK-alterations 15th International Thyroid Congress, Oct. 2015, Lake Buena Vista, Florida, Poster, 1 p.
Brzezianska, E. et al., Rearrangements of NTRK1 oncogene in papillary thyroid carcinoma, Neuroendocrinology Letters, 2007, 28(3):221-229.
Burris, H. A., III. et al., A first-in-human study of LOXO-101, a highly selective inhibitor of the tropomyosin receptor kinase (TRK) family, American Society of Clinical Oncology (ASCO) 2015 Annual Meeting, May-Jun. 2015, Chicago, IL, Poster, 1 p.
Calvo, E., Posters Discussion: Developmental Therapeutics, 2014 ESMO Congress, Sep. 26-30, 2014, 21 pp.
Cho, H. et al., Expression of mRNA for brain-derived neurotrophic factor in the dorsal root ganglion following peripheral inflammation, Brain Research, 1997, 749:358-362.
ClinicalTrials.gov, Aug. 20, 2014, A phase 1/2a study of oral RXDX-101 in adult patients with locally advanced or metastatic cancer; study targeting ALK, ROS1 or TRKA/8/C (STARTRK:1), 4 pp.
ClinicalTrials.gov, Aug. 2014, A phase 1/2a study of oral RXDX-101 in adult patients with locally advanced or metastatic cancer; study targeting ALK, ROS1 or TRKA/8/C, 36 pp.
ClinicalTrials.gov, Sep. 11, 2014, A phase 1/2a study oforal RXDX-101 in adult patients with locally advanced or metastatic cancer; study targeting ALK, ROS1 or TRKA/8/C (STARTRK-1), 7 pp.
Cohen, P., Protein kinases-the major drug targets of the twenty-first century?, Nature Reviews, Apr. 2002, Drug Discovery 1:309-315.
Cohen, P., The development and therapeutic potential of protein kinase inhibitors, Current Opinion in Chemical Biology, 1999, 3:459-465.
Collymore, D. C. et al., Genomic testing in oncology to improve clinical outcomes while optimizing utilization: the evolution of diagnostic testing, American Journal of Managed Care, Feb. 2016, 22(2):S20-S28.
Croucher et al., "TrkB inhibition by GNF-4256 slows growth and enhances chemotherapeutic efficacy in neuroblastoma xenografts", Cancer Chemother Pharmacol, 2015, 75:131-141.
Dang, C. et al., Expression of nerve growth factor receptors is correlated with progression and prognosis of human pancreatic cancer, Journal of Gastroenterology and Hepatology, 2006, 21(5):850-858.
Davidson, B. et al., Expression and activation of the nerve growth factor receptor TrkA in serous ovarian carcinoma, Clin. Cancer Res., Jun. 2003, 9:2248-2259.
Davies, K. D. et al., Resistance of ROS1 inhibition mediated by EGFR pathway activation in non-small cell lung cancer, PlOS ONE, Dec. 2013, 8(12):e82236.
Davies, K. et al., Identifying and targeting ROS1 gene fusions in non-small cell lung cancer, Clin Cancer Res, Sep. 1, 2012, 18(17):4570-4579.
De Braud, F. et al., 2014, Phase 1 open label, dose escalation study of RXDX-101, an oral pan-trk, ROS1, and ALK inhibitor, in patients with advanced solid tumors with relevant molecular alterations, Poster, 1P.
De Braud, F. et al., 2014, RXDX-101, an oral pan-TRK, POS1, and ALK inhibitor, in patients with advanced solid tumors with relevant molecular alterations, Annals of Oncology 25(Supplement 4): iv146-iv164 (abstract).
De Braud, F., 2014, Phase 1 open label, dose escalation study of RXDX-101, an oral pan-trk, ROS1, and ALK inhibitor, in patients with advanced solid tumors with relevant molecular alterations, PowerPoint presentation, ASCO 50th Annual Meeting, 18 pp.
De Melo-Jorge, M. et al., the chagas' disease parasite trypanosoma cruzi exploits nerve growth factor receptor TrkA to infect mammalian hosts, Cell Host & Microbe, Jun. 2007, 1(4):251-261.
Delafoy, L. et al., Role of nerve growth factor in the trinitrobenzene sulfonic acid-induced colonic hypersensitivity, Pain, 2003, 105:489-497.
Di Mola, F. F. et al., Nerve growth factor and Trk high affinity receptor (TrkA)gene expression in inflammatory bowel disease, Gut, 2000, 46(5):670-678.
Dionne, C. A. et al., Cell cycle-independent death of prostate adenocarcinoma is induced by the trk tyrosine kinase inhibitor CEP-751 (KT6587), Clin. Cancer Res., Aug. 1998, 4(8):1887-1898.
Doebele, R. C. et al., An oncogenic NTRK fusion in a patient with soft-tissue sarcoma with response to the tropomyosin-related kinase inhibitor LOXO-101, Cancer Discovery, Oct. 2015, 1049-1057.
Dou, Y. et. al., 2006, Increased nerve growth factor and its receptors in atopic dermatitis: an immunohistochemical study, Archives of Dermatological Research, 2008, 298(1):31-37.
Drilon et al., "Safety and Antitumor Activity of the Multitargeted Pan-TRK, ROS1, and ALK Inhibitor Entrectinib: Combined Results from Two Phase I Trials (ALKA-372-001 and STARTRK-1)", Published OnlineFirst Feb. 9, 2017, Downloaded from cancerdiscovery. aacrjournals.org on Apr. 7, 2017, pp. 401-409.
Drug Class Detail: Trk Receptor Inhibitor (Pan); https://ckb.jax.org/drugClass/show?drugClassId=Trk Receptor Inhibitor %28Pan%29: (Jul. 16, 2014).
Duffy, M. J. et al., Companion biomarkers: paving the pathway to personalized treatment for cancer, Clinical Chemistry, 2013, 59(1):1447-1456.
Freund-Michel, V. et al., The nerve growth factor and its receptors in airway inflammatory diseases, Pharmacology & Therapeutics, 2008, 117(1):52-76.

(56) References Cited

OTHER PUBLICATIONS

Gainor, Justin, MD,RXDX-101 & RXDX-102, PowerPoint Presentation, Feb. 20, 2014, 13 pp.

Greco, A. et al., Rearrangement of NKRK1 gene in papillary thyroid carcinoma, Molecular and Cellular Endocrinology, May 1, 2010, 321(1):44-49.

Hansen, K. et al., Autophagic cell death induced by TrkA receptor activation in human glioblastoma cells, Journal of Neurochemistry, 2007, 103:259-275.

Hofmann, F. et al., Blocking insulin-like growth factor-I receptor as a strategy for targeting cancer, Drug Discov Today, Aug. 2005, 10(15):1041-1047.

Hu, V. Y. et al., Decrease in bladder overactivity with ren1820 in rats with cyclophosphamide induced cystitis, The Journal of Urology, 2005, 173(3):1016-1021.

Hu, Y. et al., Identification of brain-derived neurotrophic factor as a novel angiogenic protein in multiple myeloma, Cancer Genetics and Cytogenetics, 2007, 178:1-10.

Ignyta Inc., Aug. 12, 2014, Ignyta announces second quarter 2014 company highlights and financial results, Press Release, 4 pp.

Ignyta Inc., Dec. 3, 2013, Ignyta announces completion of $54 million in private placements to catalyze precision medicine for cancer patients, Press Release, 2 pp.

Ignyta Inc., Feb. 20, 2014, Ignyta announces preliminary data from RXDX-101 phase I clinical trial, Press Release, 2 pp.

Ignyta Inc., Feb. 27, 2014, Ignyta announces of IND for RXDX-101, Press Release, 2 pp.

Ignyta Inc., Feb. 28, 2014, Ignyta announces 2013 company highlights and full year financial results, Press Release, 5 pp.

Ignyta Inc., Jul. 21, 2014, Ignyta announces initiation of STARTKR-1 global phase I/II clinical trial of RXDX-101, Press Release, 2 pp.

Ignyta Inc., May 31, 2014, Ignyta announces interim data from RXDX-101 phase I clinical trial, Press Release, 2 pp.

Ignyta Inc., May 7, 2014, Ignyta announces RXDX-101 phase I data abstract accepted for oral presentation at the 2014 ASCO annual meeting, Press Release, 2 pp.

Ignyta Inc., Nov. 1, 2013, Ignyta completes merger and announces license agreement for the development of two leading tyrosine kinase inhibitors, Press Release, 1 p.

Ignyta Inc., Nov. 18, 2014, Ignyta announces RXDX-101 phase 1 presentations at the 2014 EORTC-NCI-AACR 'molecular targets and cancer therapeutics' conference, Press Release, 2 pp.

Ignyta Inc., Nov. 7, 2014, Ignyta announces third quarter 2014 company highlights and financial results, Press Release, 5 pp.

Ignyta Inc., Sep. 15, 2014, Ignyta announces RXDX-101 phase 1 data presentation at the 2014 ESMO Congress, Press Release, 2 pp.

Ignyta Inc., Sep. 28, 2014, Ignyta announces interim data from RXDX-101 phase I clinical trial at 2014 ESMO Congress, Press Release, 2 pp.

Ignyta, Feb. 2014, Catalyzing precision medicine with integrated Rx/Ox in oncology, presentation, 23 pp.

Ignyta, Inc., Feb. 20, 2014, Form 8-K (Current Report Filing), 20 pp.

Ignyta, Inc., Jan. 13, 2014, Form 8-K (Current Report Filing), 28 pp.

Ignyta, Inc., Jun. 2, 2014, Form 8-K (Current Report Filing), 26 pp.

Ignyta, Inc., May 12, 2014, Form 8-K (Current Report Filing), 11 pp.

Ignyta, Inc., May 2, 2014, Form 8-K (Current Report Filing), 4 pp.

Ignyta, Inc., Nov. 7, 2014, Form 8-K (Current Report Filing), 13 pp.

Ignyta, Inc., Oct. 14, 2014, Form 8-K (Current Report Filing), 61 pp.

Isaacson, Jerry, Ph.D. et al., "Ignyta, Inc.: Initiation of Coverage," LifeSci Advisors Research, Feb. 14, 2014, pp. 1-37.

Iyer et al., "AZ64 inhibits TrkB and enhances the efficacy of chemotherapy and local radiation in neuroblastoma xenografts", Cancer Chemother Pharmacol, 2012, 70:477-486.

Iyer et al., "Lestaurtinib Enhances the Antitumor Efficacy of Chemotherapy in Murine Xenograft Models of Neuroblastoma", Clin Cancer Res; 2010; 16(5):1478-1485.

Iyer et al., "The TRK Inhibitor Entrectinib Enhances the Efficacy of Temozolomide and Irinotecan in a Xenograft Model of Neuroblastoma", Abstract #5390, Brochure, AACR Annual Meeting 2015 (1 page).

Jaggar, S. I. et al., Inflammation of the rat urinary bladder is associated with a referred thermal hyperalgesia which is nerve growth factor dependent, Br. J. Anaesth., 1999, 83:442-448.

Jantzen, G. M. et al., "Sustained- and controlled-release drug delivery systems", in Banker et al. eds., Modern Pharmaceutics, 1996, 3rd Ed. pp. 575-609, Marcel Dekker, Inc., New York, NY.

Johnson, T. W. et al., Discovery of (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (PF-06463922), a macrocyclic inhibitor of anaplastic lymphoma kinase (ALK) and c-ros oncogene 1(ROS1) with preclinical brain exposure and broad-spectrum potency against ALK-resistant mutations, Journal of Medicinal Chemistry, 2014, 57(11);4720-4744.

Karaman, M. W. et al., A quantitative analysis of kinase inhibitor selectivity, Nature Biotechnology, Jan. 2008, 26(1):127-132.

Khandwala, H. M. et al., The effects of insulin-like growth factors on tumorigenesis and neoplastic growth, Endocr Rev, 2000, 21(3):215-244.

Kruettgen, A. et al., The dark side of the NGF family: neurotrophins in neoplasias, Brain Pathology, 2006, 16:304-310.

Kushner, BH, et al. Irinotecan plus temozolomide for relapsed or refractory neuroblastoma. J Clin Oncol. Nov. 20, 2006;24(33):5271-6.

Lamant et al., 2000, Expression of the ALK tyrosine kinase gene in neuroblastoma, American Journal of Pathology, 156:1711-1721.

Lamb, K. et al., Nerve growth factor and gastric hyperalgesia in the rat, Neurogastroenterol. Motil, 2003, 15:355-361.

Laron, Z., Laron syndrome (primary growth hormone resistance or insensitivity): the personal experience 1958-2003, J Clin Endocrinol Metab, 2004, 89(3):1031-1044.

Le Roith, D. et al., The somatomedin hypothesis: 2001, Endocr Rev, 2001, 22(1):53-74.

Lee, J. et al., Identification of ROS1 rearrangement in gastric adenocarcinoma, Cancer, May 1, 2013, 119:1627-1635.

Li, Q. et al., Brain derived neurotrophic factor (BDNF) contributes to the pain hypersensitivity following surgical incision in the rats, Molecular Pain, 2008, 4:27, 11 pp.

Li, T. et al., Genotyping and genomic profiling of Non-Small-Cell lung cancer: implications for current and future therapies, Journal of Clinical Oncology, Mar. 10, 2013, vol. 31, No. 8, pp. 1039-1049.

Lindeman, N. I., MD et al., Molecular testing guideline for selection of lung cancer patients for EGFR and ALK tyrosine kinase inhibitors, Journal of Thoracic Oncology, Jul. 2013, 8(7):823-859.

Lipska, B. S. et al., c.1810C>T polymorphism of NTRK1 gene is associated with reduced survival in neuroblastoma patients, BMC Cancer, Biomed Central, Dec. 13, 2009, London, GB, 9(1):436.

Ma, Q. et al., The progressive tactile hyperalgesia induced by peripheral inflammation is nerve growth factor dependent, Neuroreport, 1997, 8(4):807-810.

Marchetti, A. et al., Frequent mutations in the neurotrophic tyrosine receptor kinase gene family in large cell neuroendocrine carcinoma of the lung, Human Mutation, 2008, 29(5):609-616.

Marsilje, T. H. et al., Synthesis, structure-activity relationships and in vivo efficacy of the novel potent and selective anaplastic lymphoma kinase (ALK) inhibitor LDK378 currently in phase 1 and 2 clinical trials, J. Med. Chem., 2013, 56:5675-5690 and Supporting Information.

Matayoshi, S. et al., Actions of brain-derived neurotrophic factor on spinal nociceptive transmission during inflammation in the rat, J. Physiol., 2005, 569(2):685-695,.

McMahon, S. B. et al., The biological effects of endogenous nerve growth factor on adult sensory neurons revealed by a trkA-IgG fusion molecule, Nat. Med., Aug. 1995, 1(8):774-780.

Meyer, J. et al., Remarkable leukemogenic potency and quality of a constitutively active neurotrophin receptor, ΔTrkA, Leukemia, 2007, 21:2171-2180.

Milkeiwicz, K. L. et al., Inhibitors of anaplastic lymphoma kinase: a patent review, Expert Opin. Ther. Patents, 2010, 20(12):1653-1681.

(56) References Cited

OTHER PUBLICATIONS

Minturn et al, "Phase I trial of lestaurtinib for children with refractory neuroblastoma: a new approaches to neuroblastoma therapy consortium study," Cancer Chemother Pharmacol, Feb. 22, 2011, 9 pages.
Molina-Vila, M. A. et al., Impact of the new EGF receptor and ALK testing guideline on personalized lung cancer medicine, Personalized Medicine, 2013, 19(5):415-417.
Murphy et al., "Monitoring activity of RXDX-101 in Phase 1/2 patients using a pharmacodynamics assay for TrkA activation", European Journal of Cancer, Poster Session—Molecular Targeted Agents II, 2014, 50(6):143-144.
Nakagawara et al.; "Association between high levels of expression of the Trk gene and favorable outcome in human neuroblastoma"; N Engl J Med; 1993; 328:847-54.
Nakagawara, A., Trk receptor tyrosine kinases: a bride between cancer and neural development, Cancer Letters, 2001, 169:107-114.
National Comprehensive Cancer Network, NCCN Clinical Practice Guidelines in Oncology: Non-small cell lung cancer, Apr. 2016, Version 4.2016. 169 pp.
Okimoto, R. A. et al., Recent advances in personalized lung cancer medicine, Personalized Medicine, 2014, 11(3):309-321.
Patapoutian, A. et al., Trk receptors: mediators of neurotrophin action, Current Opinion in Neurobiology, 2001, 11:272-280.
PCT International Search Report and Written Opinion for Application No. PCT/US2015/062975, dated Feb. 12, 2016. (16 pages).
PCT International Preliminary Report on Patentability (Chapter 1) for Application No. PCT/US2015/062975 dated Jun. 15, 2017.(9 pages).
PCT International Search Report for international application No. PCT/EP2015/053544 dated Mar. 30, 2015. (4 pages).
PCT Written Opinion of the International Searching Authority for International Application No. PCT/EP2015/053544 dated Aug. 27, 2015. (6 pages).
Perez-Pinera,P. et al., The Trk tyrosine kinase inhibitor K252a regulates growth on lung adenocarcinomas, Molecular and Cellular Biochemistry, 2007, 295:19-26.
Pierotti, A. et al., Oncogenic rearrangements of the NRTK1/NGF receptor, Cancer Letters, 2006, 232:90-98.
Pinski, J. et al., Trk receptor inhibition induced apoptosis of proliferating but not quiescent human osteoblasts, Cancer Research, Feb. 15, 2002, 62:986-989.
Puig De La Bellacasa, R. et al., ALK and ROS1 as a joint target for the treatment of lung cancer: a review, Translational Lung Cancer Research, 2013, vol. 2, No. 2, pp. 72-86.
Raychaudhuri, S. P. et al., K252a, a high-affinity nerve growth factor receptor blocker, improves psoriasis: an in vivo study using the severe combined immunodeficient mouse-human skin model, Journal of Investigative Dermatology, Mar. 3, 2004, 122(3);812-819.
Sakamoto, H. et al., CH5424802, a selective ALK inhibitor capable of blocking the resistant gatekeeper mutant, Cancer Cell, 2011, 19:679-690.
Shaw, A. T. et al., Crizotinib versus chemotherapy in advanced ALK-positive lung cancer, The New England Journal of Medicine, Jun. 30, 2013, 268(25):2385-2394.
Shaw, A. T. et al., Targeting anaplastic lymphoma kinase in lung cancer, Clin. Cancer Res., 2011, 17:2081-2086.
Shelton, D. et al., Nerve growth factor mediates hyperalgesia and cachexia in auto-immune arthritis, Pain, 2005, 116:8-16.
Sohrabji, F. et al., Estrogen-BDNF interactions: implications for neurodegenerative diseases, Neuroendocrinology, 2006, 27(4):404-414.
Stumpfova, M. et al., Zeroing in on ROS1 rearrangements in non-small cell lung cancer, Clin Cancer Res, Aug. 2, 2012, 18(16):4222-4224.
Tatematsu, T. et al., Investigation of neurotrophic tyrosine kinase receptor 1 fusions and neurotrophic tyrosine kinase receptor family expression in non-small-cell lung cancer and sensitivity to AZD7451 in vitro, Molecular and Clinical Oncology, 2014, 2:725-730.
Thompson S. W. N. et al., Brain-derived neurotrophic factor is an endogenous modulator of nociceptive responses in the spinal cord, Proc. Natl. Acad. Sci. USA, Jul. 1999, 96:7714-7718.
Tremodar PI-2, Highlights or Prescribing Information, 2014. (17 pages).
Truzzi, F. et al., Neurotrophins and their receptors stimulate melanoma cell proliferation and migration, Journal of Investigative Dermatology, 2008, 128(8):2031-2040.
Tzelepi, V., Editorial: Personalized cancer treatment, Current Molecular Pharmacology, 2014, 7(1), 2 pp.
U.S. Office Action for U.S. Appl. No. 14/623,904 dated Oct. 16, 2015. (10 pages).
U.S. Office Action for U.S. Appl. No. 14/623,904 dated Feb. 4, 2016.(8 pages).
U.S. Office Action for U.S. Appl. No. 14/623,904 dated Jun. 7, 2016. (14 pages).
U.S. Office Action for U.S. Appl. No. 14/623,904 dated Sep. 16, 2016. (12 pages).
U.S. Office Action for U.S. Appl. No. 14/623,904 dated Dec. 9, 2016. (16 pages).
U.S. Office Action for U.S. Appl. No. 14/623,904 dated Apr. 28, 2017. (18 pages).
U.S. Office Action for U.S. Appl. No. 14/623,904 dated Nov. 3, 2017. (19 pages).
U.S. Office Action for U.S. Appl. No. 14/623,904 dated Mar. 26, 2018. (12 pages).
U.S. Office Action for U.S. Appl. No. 14/953,969 dated Feb. 24, 2017. (8 pages).
U.S. Office Action for U.S. Appl. No. 14/953,969 dated Oct. 2, 2017. (21 pages).
U.S. Notice of Allowance for U.S. Appl. No. 14/953,969 dated May 2, 2018. (10 pages).
U.S. Office Action for U.S. Appl. No. 15/114,367 dated Jan. 30, 2017. (7 pages).
U.S. Office Action for U.S. Appl. No. 15/114,367 dated Jun. 15, 2017. (12 pages).
U.S. Office Action for U.S. Appl. No. 15/114,367 dated Feb. 2, 2018. (21 pages).
Vaishnavi, A. et al., Oncogenic and drug sensitive NTRK1 rearrangements in lung cancer, Nat Med., Nov. 2013, 19(11):1469-1472.
Valent, A. et al. Mapping of the tyrosine kinase receptors trkA (NTRK1), trkB (NTRK2) and trkC(NTRK3) to human chromosomes 1q22, 9q22 and 15q25 by fluorescence in situ hybridization. Eur.J. Hum. Genet (1997), vol. 5(2), pp. 102-104.
Valentinis, B. et al., IGF-I receptor signaling in transformation and differentiation, 2001, Mol Pathol, 54:133-137.
Voskoglou-Nomikos, T. et al., Clinical predictive value of the in vitro cell line, human xenograft, and mouse allograft preclinical cancer models, Clinical Cancer Research, Sep. 15, 2003, 9:4227-4239.
Wang, Y. et al., Insulin-like growth factor receptor-1 as an anticancer target: blocking transformation and inducing apoptosis, Curr Cancer Drug Targets, 2002, 2:191-207.
Warner, S. et al., Targeting aurora-2 kinase in cancer, Molecular Cancer Therapeutics, Jun. 3, 2003, 2:589-595.
Weroha, S. J. et al., IFG-1 receptor inhibitors in clinical trials-early lessons, J. Mammary Gland Biol. Neoplasia, 2008, vol. 13, pp. 471-483.
Wolff, M.E., Burger's Medicinal Chemistry and Drug Discovery, 5th Ed. vol. 1, 1995, pp. 975-977, John Wiley & Sons, Inc., New York, NY.
Wood et al., "Somatic Mutations of GUCY2F, EPHA3, and NTRK3 in Human Cancers", Human Mutation in Brief #923, 2006. (9 pages).
Woolf, C. J. et al., Letter to Neuroscience: Nerve growth factor contributes to the generation of inflammatory sensory hypersensitivity, Neuroscience, 1994, vol. 62, No. 2, pp. 327-331.
Xalkori® (crizotinib) capsules, for oral use, Prescribing Information, Mar. 2016, 27 pp.
Zahn, P. et al., Effect of blockade of nerve growth factor and tumor necrosis factor on pain behaviors after plantar incision, J. Pain, vol. 5 No. 3, Apr. 2004, pp. 157-163.

(56) References Cited

OTHER PUBLICATIONS

Zhu, L., et al. Implications of tropomyosin-related kinase B (TrkB) in head and neck cancer. Anticancer Res. Sep.-Oct. 2007;27(5A):3121-6.
Zykadia™ (ceritinib) capsules, for oral use, Prescribing Information, Apr. 2014, 16 pp.
U.S. Notice of Allowance for U.S. Appl. No. 14/623,904 dated Oct. 17, 2018, 9 pages.
U.S. Appl. No. 16/249,703, filed Jan. 16, 2019, Ignyta, Inc.
Estrada-Bernal et al., "TRK kinase domain mutations that induce resistance to a pan-TRK inhibitor", [abstract]. In: Proceedings of the AACR-NCI-EORTC International Conference: Molecular Targets and Cancer Therapeutics; Nov. 5-9, 2015; Boston, MA. Philadelphia (PA): AACR; Mol Cancer Ther 2015;14(12 Suppl 2):Abstract nr C65.
Extended European Search Report issued in European Patent Application No. 16804039.2 dated Nov. 16, 2018.
Gad et al., "Neurotrophic activities of trk receptors conserved over 600 million years of evolution", J. Neurobiol., 2004;60(1):12-20.
Iannone et al., "Increased expression of nerve growth factor (NGF) and high affinity NGF receptor (p140 TrkA) in human osteoarthritic chondrocytes", Rheumatology, 2002;41:1413-1418.
International Preliminary Report on Patentability (Chapter 1) for Application No. PCT/US2015/062975 dated Jun. 15, 2017.
International search report issued in PCT/US2018/042756 dated Nov. 12, 2018.
Lee et al., "Mechanisms of Constitutive Activation of Janus Kinase 2-V617F Revealed at the Atomic Level Through Molecular Dynamics Simulations 1," Cancer, vol. 115, No. 8, pp. 1692-1700 (2009).
Lewis et al., "The Discovery and Optimization of a Novel Class of Potent, Selective, and Orally Bioavailable Anaplastic Lymphoma Kinase (ALK) Inhibitors with Potential Utility for the Treatment of Cancer", Journal of Medicinal Chemistry, 2012;55(14): 6523-6540.
Li et al., "Abstract A173: Potent anti-tumor activity of entrectinib in patient-derived models harboring oncogenic gene rearrangements of NTRKs," Molecular Cancer Therapeutics, (2015), 14(12):Supplement 2, p. A173.
Omura et al., "A New Alkaloid AM-2282 of Streptomyces Origin Taxonomy, Fermentation, Isolation and Preliminary Characterization", Journal of Antibiotics, 1977, 30(4):275-282.
Pardue et al., "Nucleic Acid Hybridization. A practical approach", IRL Press, Oxford Washington/DC. 1985:170-203.
PCT International Preliminary Report on Patentability (Chapter 1) for PCT/US2016/034166 dated Dec. 14, 2017. (10 pages).
PCT International Preliminary Report on Patentability (Chapter II) for Application No. PCT/US2016/066919, dated Dec. 7, 2017. (22 pages).
PCT International Search Report and Written Opinion dated Apr. 21, 2017 in PCT Patent Application No. PCT/US2016/066919.
PCT International Search Report and Written Opinion for PCT/US2016/034166 dated Oct. 19, 2016. (18 pages).
Russo et al., "Acquired Resistance to the TRK Inhibitor Entrectinib in Colorectal Cancer," Cancer Discovery, (2016), 6:36-44.
Uniprot Accession P04629. "NTRK1_human", (Jun. 24, 2015), available on the internet: http://www.uniprot.org/uniprot/P04629.txt?version=204 (12 pages).
Wei et al., "Abstract 2136: Entrectinib is effective against the gatekeeper and other emerging resistance mutations in NTRK-, ROS1- and ALK-rearranged cancers", [abstract], Proceedings: AACR 107th Annual Meeting 2016; Apr. 16-20, 2016: New Orleans, LA; 2016;76(14 Suppl):Abstract nr 2136.
Zhu et al., "Nerve Growth Factor Expression Correlates With Perineural Invasion and Pain in Human Pancreatic Cancer", Journal of Clinical Oncology, 1999;17:2419-2428.
Iyer et al., "Abstract 5390: The TRK Inhibitor RXDX-101 enhances the efficacy of temozolomide and irinotecan in a xenograft model of neuroblastoma," Cancer Research, Aug. 1, 2015, vol. 75, Iss. 15, Supplement, p. 5390.
International Search Report and Written Opinion issued in PCT/IB2018/058031 dated Feb. 12, 2019.
Vasconcelos et al., "Solid dispersions a strategy to improve oral bioavailability of poor water soluble drug," Drug Discovery Today, vol. 12, Jan. 2012, pp. 1068-1075.

ns, E. et al. Cancer Res (2008) 68:(2) 346-351) (Truzzi et

COMBINATIONS FOR THE TREATMENT OF NEUROBLASTOMA

CROSS-REFERENCE TO RELATED APPLICATIONS

This application is a continuation of U.S. patent application Ser. No. 14/953,969, filed Nov. 30, 2015; which claims the benefit of U.S. Provisional Application No. 62/086,366, filed on Dec. 2, 2014; each of which is incorporated herein by reference in its entirety; including any drawings.

FIELD

The present disclosure relates to certain substituted indazole compounds, which modulate the activity of protein kinases. The compounds of this disclosure are therefore useful in treating diseases caused by deregulated protein kinase activity. The present disclosure also provides methods for preparing these compounds, pharmaceutical compositions comprising these compounds, and methods of treating diseases utilizing pharmaceutical compositions comprising these compounds.

BACKGROUND

The malfunctioning of protein kinases (PKs) is the hallmark of numerous diseases. A large share of the oncogenes and proto-oncogenes involved in human cancers encode for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or deregulation see, for instance, Current Opinion in Chemical Biology 1999, 3:459-465.

Neuroblastoma, a pediatric malignancy of the sympathetic nervous system, is characterized by clinical and biological heterogeneity. Approximately one-half of neuroblastoma patients present with advanced-stage disease, and despite intensive multimodality therapy, including myeloablative regimens, survival for these children is less than 40%. Identification of tumor targets and advances in target-specific therapies with minimal non-specific toxicity are needed for this patient population. The Trk family of receptor tyrosine kinases is critical for neuronal survival and differentiation during the development of the nervous system. The Trk receptors are differentially expressed in human neuroblastoma and likely play a central role in tumorigenesis and/or cell survival. TrkA is highly expressed by neuroblastomas with favorable biological and clinical features, and expression is associated with patient outcome. In contrast, TrkB expression is restricted to a malignant subset of neuroblastomas. Co-expression of TrkB and its ligand, BDNF, in the majority of neuroblastomas, provides a potential autocrine survival pathway in biologically aggressive, high-risk tumors. Additionally, the recent identification of a constitutively active TrkA splice variant (TrkAIII) that is preferentially expressed in advanced-staged tumors highlights the complex role of Trk signaling in neuroblastoma biology and its potential as a therapeutic target.

Neurotrophin signaling through the Trk family of receptor tyrosine kinases (RTKs) plays a critical role in the development, maintenance and function of the nervous system. Activation of these receptors regulates cell survival, proliferation, migration, differentiation, and apoptosis during development. They exert this influence by modulating the responses of neurons to the neurotrophin family of growth factors in a temporally and spatially regulated manner. The neurotrophins nerve growth factor (NGF), brain-derived neurotrophic factor (BDNF), and neurotrophin-3 (NT3) are the cognate ligands for TrkA (NTRK1), TrkB (NTRK2), and TrkC (NTRK3), respectively.

Neuroblastoma, a common pediatric tumor of the postganglionic sympathetic nervous system, provides an ideal model for the study of Trk signaling and inhibition in cancer. Neuroblastomas are characterized by clinical heterogeneity, from spontaneous regression in infants to relentless progression in older children. The prognosis for these latter patients remains poor, with three-year event-free survival (EFS) probabilities of 30-40% (5-7). Indeed, neuroblastomas can be classified into distinct subsets based on genetic alterations and biologic features (8), and the expression of Trk receptors likely contributes to these distinct behaviors.

Expression of TrkA in neuroblastoma cell lines has been shown to mediate neuronal differentiation, growth arrest and inhibition of angiogenesis in response to NGF. In contrast, unfavorable neuroblastomas frequently express TrkB and its ligand BDNF, which together comprise an autocrine or paracrine survival pathway. These tumors typically have gross segmental chromosomal aberrations including amplification of the MYCN proto-oncogene. The TrkB/BNDF pathway promotes cell survival, protects cells from injury, and blocks chemotherapy-mediated cell death in vitro. Although a number of genes are likely involved in the development and clinical behavior of favorable and unfavorable neuroblastomas, the pattern of Trk gene expression (TrkA versus TrkB) likely plays a role.

Recent literature has also shown that overexpression, activation, amplification and/or mutation of Trk's are associated with many cancers including neuroblastoma (Brodeur, G. M., Nat. Rev. Cancer 2003, 3, 203-216), ovarian cancer (Davidson. B., et al., Clin. Cancer Res. 2003, 9, 2248-2259), breast cancer (Kruettgen et al, Brain Pathology 2006, 16: 304-310), prostate cancer (Dionne et al, Clin. Cancer Res. 1998, 4(8): 1887-1898), pancreatic cancer (Dang et al, Journal of Gastroenterology and Hepatology 2006, 21(5): 850-858), multiple myeloma (Hu et al, Cancer Genetics and Cytogenetics 2007, 178: 1-10), astrocytoma and medulloblastoma (Kruettgen et al, Brain Pathology 2006, 16: 304-310) glioma (Hansen et al, Journal of Neurochemistry 2007, 103: 259-275), melanoma (Truzzi et al, Journal of Investigative Dermatology 2008, 128(8): 2031-2040), thyroid carcinoma (Brzezianska et al, Neuroendocrinology Letters 2007, 28(3), 221-229.), lung adenocarcinoma (Perez-Pinera et al, Molecular and Cellular Biochemistry 2007, 295(1&2), 19-26), large cell neuroendocrine tumors (Marchetti et al, Human Mutation 2008, 29(5), 609-616), and colorectal cancer (Bardelli, A., Science 2003, 300, 949).

In preclinical models of cancer, Trk inhibitors are efficacious in both inhibiting tumor growth and stopping tumor metastasis. In particular, non-selective small molecule inhibitors of Trk A, B and C and Trk/Fc chimeras were efficacious in both inhibiting tumor growth and stopping tumor metastasis (Nakagawara, A. (2001) Cancer Letters 169:107-114; Meyer, J. et al. (2007) Leukemia, 1-10; Pierottia, M. A. and Greco A., (2006) Cancer Letters 232:90-98; Eric Adriaensal, Journal of Investigative Dermatology 2008, 128(8): 2031-2040. Therefore, an inhibitor of the Trk family of kinases is expected to have utility in the treatment of cancer.

Various gene rearrangements of the Trk gene have been implicated in human malignancies. For example, the MPRIP-NTRK1 and CD74-NTRK1 gene rearrangements have been implicated in the development of non-small cell lung cancer. Gene rearrangements TPM3-NTRK1, TGF-NTRK1 and TPR-NTRK1 have been implicated in the development of papillary thyroid cancer. The TPM3-NTRK1 gene rearrangement has been implicated in the development of colorectal cancer. NTRK1, NTRK2 or NTRK3 gene rearrangements have also been identified in glioblastoma, AML and secretory breast cancer. In 2013, Vaishnavi et al. reported novel NTRK1 fusions in 3/91 pan-negative patients with lung adenocarcinoma using NGS and FISH (Vaishnavi et al. Nat Med. 2013 November; 19(11):1469-72).

SUMMARY

There is a need for improved methods of treating patients that are suffering with neuroblastomas that demonstrate increased efficacy and/or decreased toxicity compared to present methods of treating such patients. Disclosed herein are methods for treating neuroblastoma in a patient, comprising administering to the patient a therapeutically effective amount of at least one compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino)benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, in combination with at least one different chemotherapeutic agent. Also disclosed herein are pharmaceutical compositions, comprising (1) at least one compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, (2) at least one different chemotherapeutic agent, and (3) at least one pharmaceutically acceptable excipient.

DETAILED DESCRIPTION

Figure 1:
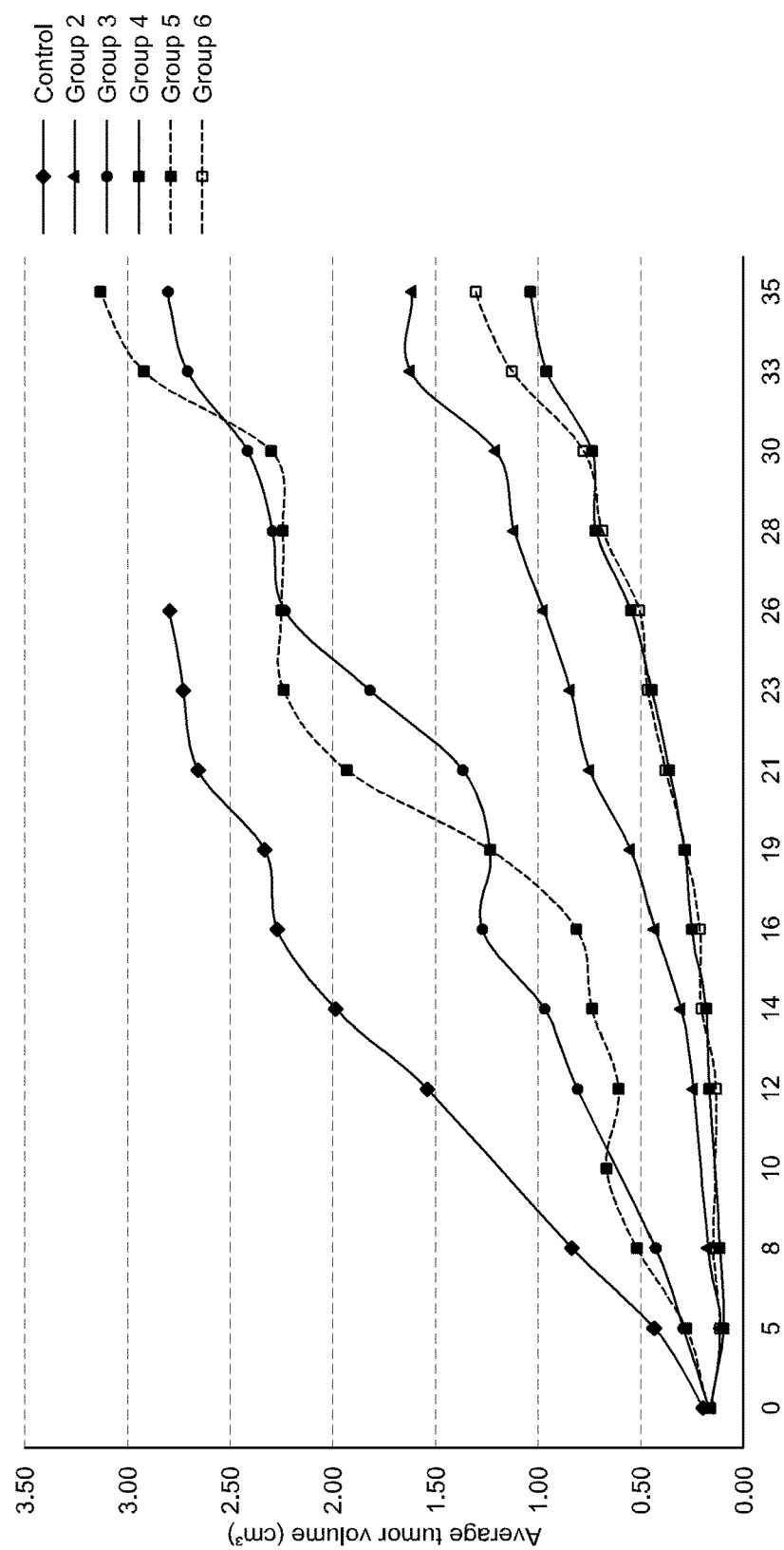
FIG. 1 shows the growth of tumors on animals treated with (1) Group 1: control (treated with vehicle alone) (solid line with diamonds); (2) Group 5: a combination of irinotecan and temozolomide (both oral, once per day, 5 times per week on weeks 1, 3, and 5) alternating with treating with N-[5-(3,5-difluorobenzyl)-1H-indazol-3-yl]-4-(4-methyl-piperazin-1-yl)-2-(tetrahydro-2H-pyran-4-ylamino) benzamide (oral, 60 mg per kg, twice a day, 7 times per week on weeks 2, 4, and 6) (dotted line with solid squares; solid bars represent period of dosing with N-[5-(3,5-difluorobenzyl)-1H-indazol-3-yl]-4-(4-methyl-piperazin-1-yl)-2-(tetrahydro-2H-pyran-4-ylamino) benzamide on weeks 2, 4 and 6); (3) Group 3: irinotecan and temozolomide (both oral, once per day, 5 times per week) (solid line with solid circles); (4) Group 2: N-[5-(3,5-difluorobenzyl)-1H-indazol-3-yl]-4-(4-methyl-piperazin-1-yl)-2-(tetrahydro-2H-pyran-4-ylamino) benzamide alone (oral, 60 mg per kg, twice per day, 7 times per week) (solid line with triangles); (5) Group 6: N-[5-(3,5-difluorobenzyl)-1H-indazol-3-yl]-4-(4-methyl-piperazin-1-yl)-2-(tetrahydro-2H-pyran-4-ylamino) benzamide (oral, 60 mg per kg, twice per day, 7 times per week throughout the study) plus irinotecan and temozolomide (both oral, once per day, 5 times per week on weeks 1, 3 and 5) (dotted line with open squares); and (6) Group 4: N-[5-(3,5-difluorobenzyl)-1H-indazol-3-yl]-4-(4-methyl-piperazin-1-yl)-2-(tetrahydro-2H-pyran-4-ylamino) benzamide (oral, 60 mg per kg, twice per day, 7 times per week throughout the study), plus irinotecan and temozolomide (both oral, once per day, 5 times per week throughout the study) (solid line with solid squares).

The preparation and use of compounds N-[5-(3,5-difluorobenzyl)-1H-indazol-3-yl]-4-(piperazin-1-yl)-2-(tetrahydro-2H-pyran-4-ylamino) benzamide and N-[5-(3,5-difluorobenzyl)-1H-indazol-3-yl]-4-(4-methyl-piperazin-1-yl)-2-(tetrahydro-2H-pyran-4-ylamino) benzamide as inhibitors of anaplastic lymphoma kinase are described in U.S. Pat. No. 8,299,057, issued Oct. 30, 2012, the disclosure of which is hereby incorporated by reference in its entirety.

The preparation and use of compound N-[5-(3,5-difluoro-benzenesulfonyl)-1H-indazol-3-yl]-2-((R)-2-methoxy-1-methyl-ethylamino)-4-(4-methyl-piperazin-1-yl) benzamide are described in U.S. Pat. No. 8,114,865, issued Feb. 14, 2012, the disclosure of which is hereby incorporated by reference in its entirety.

In some embodiments are provided methods for treating neuroblastoma in a patient, the method comprising administering to the patient a therapeutically effective amount of at least one compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3, 5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, in combination with at least one chemotherapeutic agent. In some embodiments said neuroblastoma is tropomyosin-receptor-kinase positive. In some embodiments are provided such methods, wherein the compound administered to the patient in combination with at least one chemotherapeutic agent is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof. In some embodiments are provided such methods, wherein the at least one chemotherapeutic agent comprises at least one topoisomerase I inhibitor. In some embodiments are provided such methods, wherein the at least one chemotherapeutic agent comprises at least one alkylating agent. In some embodiments are provided such methods, wherein the at least one chemotherapeutic agent comprises at least one topoisomerase I inhibitor and at least one alkylating agent. In some embodiments are provided such methods, wherein the at least one topoisomerase I inhibitor is irinotecan. In some embodiments are provided such methods, wherein the at least one alkylating agent is temozolomide. In some embodiments are provided such methods, wherein the tropomyosin-receptor-kinase is at least one of TrkA, TrkB, and TrkC. In some embodiments are provided such methods, wherein the tropomyosin-receptor-kinase is TrkA. In some embodiments are provided such methods, wherein the tropomyosin-receptor-kinase is TrkB. In some embodiments are provided such methods, wherein the tropomyosin-receptor-kinase is TrkC. In some embodiments are provided such methods, wherein the tropomyosin-receptor-kinases are TrkA and Trk B. In some embodiments are provided such methods, wherein the tropomyosin-receptor-kinases are TrkA and Trk C. In some embodiments are provided such methods, wherein the tropomyosin-receptor-kinases are TrkB and Trk C. In some embodiments are provided such methods, wherein the tropomyosin-receptor-kinases are TrkA and Trk B and TrkC.

In some embodiments are provided methods for treating neuroblastoma in a patient, wherein the neuroblastoma is tropomyosin-receptor-kinase positive, comprising administering to the patient a therapeutically effective amount of at least one compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, in combination with at least one chemotherapeutic agent. In some embodiments are provided such methods, wherein the compound administered to the patient in combination with at least one chemotherapeutic agent is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof. In some embodiments are provided such methods, wherein the at least one chemotherapeutic agent comprises at least one topoisomerase I inhibitor. In some embodiments are provided such methods, wherein the at least one chemotherapeutic agent comprises at least one alkylating agent. In some embodiments are provided such methods, wherein the at least one chemotherapeutic agent comprises at least one topoisomerase I inhibitor and at least one alkylating agent. In some embodiments are provided such methods, wherein the at least one topoisomerase I inhibitor is irinotecan. In some embodiments are provided such methods, wherein the at least one alkylating agent is temozolomide. In some embodiments are provided such methods, wherein the tropomyosin-receptor-kinase is at least one of TrkA, TrkB, and TrkC. In some embodiments are provided such methods, wherein the tropomyosin-receptor-kinase is TrkA. In some embodiments are provided such methods, wherein the tropomyosin-receptor-kinase is TrkB. In some embodiments are provided such methods, wherein the tropomyosin-receptor-kinase is TrkC.

In some embodiments are provided methods for treating neuroblastoma in a patient, the method comprising: (1) testing one or more cells comprising the neuroblastoma in the patient for the presence of tropomyosin-receptor-kinase; and (2) administering to the patient an effective amount of at least one compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, in combination with at least one chemotherapeutic agent if said one or more cells tests positive for tropomyosin-receptor-kinase. In some embodiments are provided such methods, wherein the compound administered to the patient in combination with at least one chemotherapeutic agent is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof. In some embodiments are provided such methods, wherein the at least one chemotherapeutic agent comprises at least one topoisomerase I inhibitor. In some embodiments are provided such methods, wherein the at least one chemotherapeutic agent comprises at least one alkylating agent. In some embodiments are provided such methods, wherein the at least one chemotherapeutic agent comprises at least one topoisomerase I inhibitor and at least one alkylating agent. In some embodiments are provided such methods, wherein the at least one topoisomerase I inhibitor is irinotecan. In some embodiments are provided such methods, wherein the at least one alkylating agent is temozolomide. In some embodiments are provided such methods, wherein the tropomyosin-receptor-kinase is at least one of TrkA, TrkB, and TrkC. In some embodiments are provided such methods, wherein the tropomyosin-receptor-kinase is TrkA. In some embodiments are provided such methods, wherein the tropomyosin-receptor-kinase is TrkB. In some embodiments are provided such methods, wherein the tropomyosin-receptor-kinase is TrkC. In some embodiments are provided such methods, wherein the tropomyosin-receptor-kinases are TrkA and Trk B. In some embodiments are provided such methods, wherein the tropomyosin-receptor-kinases are TrkA and Trk C. In some embodiments are provided such methods, wherein the tropomyosin-receptor-kinases are TrkB and Trk C. In some embodiments are provided such methods, wherein the tropomyosin-receptor-kinases are TrkA and Trk B and TrkC.

In some embodiments are provided methods for treating tropomyosin-receptor-kinase positive neuroblastoma in a patient, comprising administering to said patient a therapeutically effective amount of at least one compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, in combination with at least one chemotherapeutic agent. In some embodiments are provided such methods, wherein the compound administered to the patient in combination with at least one chemotherapeutic agent is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof. In some embodiments are provided such methods, wherein the at least one chemotherapeutic agent comprises at least one topoisomerase I inhibitor. In some embodiments are provided such methods, wherein the at least one chemotherapeutic agent comprises at least one alkylating agent. In some embodiments are provided such methods, wherein the at least one chemotherapeutic agent comprises at least one topoisomerase I inhibitor and at least one alkylating agent. In some embodiments are provided such methods, wherein the at least one topoisomerase I inhibitor is irinotecan. In some embodiments are provided such methods, wherein the at least one alkylating agent is temozolomide. In some embodiments are provided such methods, wherein the tropomyosin-receptor-kinase is at least one of TrkA, TrkB, and TrkC. In some embodiments are provided such methods, wherein the tropomyosin-receptor-kinase is TrkA. In some embodiments are provided such methods, wherein the tropomyosin-receptor-kinase is TrkB. In some embodiments are provided such methods, wherein the tropomyosin-receptor-kinase is TrkC. In some embodiments are provided such methods, wherein the at least one tropomyosin-receptor-kinase are TrkA and Trk B. In some embodiments are provided such methods, wherein the at least one tropomyosin-receptor-kinase are TrkA and Trk C. In some embodiments are provided such methods, wherein the at least one tropomyosin-receptor-kinase are TrkB and Trk C. In some embodiments are provided such methods, wherein the at least one tropomyosin-receptor-kinase are TrkA and Trk B and TrkC.

In some embodiments are provided methods for treating neuroblastoma in a patient, comprising administering to the patient a therapeutically effective amount of at least one compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, in combination with at least one chemotherapeutic agent, and wherein one or more cells comprising the neuroblastoma is determined to be positive for tropomyosin-receptor-kinase. In some embodiments are provided such methods, wherein the compound administered to the patient in combination with at least one chemotherapeutic agent is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof. In some embodiments are provided such methods, wherein the at least one chemotherapeutic agent comprises at least one topoisomerase I inhibitor. In some embodiments are provided such methods, wherein the at least one chemotherapeutic agent comprises at least one alkylating agent. In some embodiments are provided such methods, wherein the at least one chemotherapeutic agent comprises at least one topoisomerase I inhibitor and at least one alkylating agent. In some embodiments are provided such methods, wherein the at least one topoisomerase I inhibitor is irinotecan. In some embodiments are provided such methods, wherein the at least one alkylating agent is temozolomide. In some embodiments are provided such methods, wherein the tropomyosin-receptor-kinase is at least one of TrkA, TrkB, and TrkC. In some embodiments are provided such methods, wherein the tropomyosin-receptor-kinase is TrkA. In some embodiments are provided such methods, wherein the tropomyosin-receptor-kinase is TrkB. In some embodiments are provided such methods, wherein the tropomyosin-receptor-kinase is TrkC. In some embodiments are provided such methods, wherein the at least one tropomyosin-receptor-kinase are TrkA and Trk B. In some embodiments are provided such methods, wherein the at least one tropomyosin-receptor-kinase are TrkA and Trk C. In some embodiments are provided such methods, wherein the at least one tropomyosin-receptor-kinase are TrkB and Trk C. In some embodiments are provided such methods, wherein the at least one tropomyosin-receptor-kinase are TrkA and Trk B and TrkC.

In some embodiments are provided methods for treating neuroblastoma in a patient, comprising (a) acquiring knowledge that one or more cells comprising the neuroblastoma are tropomyosin-receptor-kinase positive, (b) selecting a compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, as a treatment for the patient, based on the recognition that the compound is effective in treating the neuroblastoma in the patient; and (c) administering a therapeutically effective amount of least one of the compounds to the neuroblastoma patient in combination with at least one chemotherapeutic agent. In some embodiments are provided such methods, wherein the compound administered to the patient in combination with at least one chemotherapeutic agent is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof. In some embodiments are provided such methods, wherein the at least one chemotherapeutic agent comprises at least one topoisomerase I inhibitor. In some embodiments are provided such methods, wherein the at least one chemotherapeutic agent comprises at least one alkylating agent. In some embodiments are provided such methods, wherein the at least one chemotherapeutic agent comprises at least one topoisomerase I inhibitor and at least one alkylating agent. In some embodiments are provided such methods, wherein the at least one topoisomerase I inhibitor is irinotecan. In some embodiments are provided such methods, wherein the at least one alkylating agent is temozolomide. In some embodiments are provided such methods, wherein the tropomyosin-receptor-kinase is at least one of TrkA, TrkB, and TrkC. In some embodiments are provided such methods, wherein the tropomyosin-receptor-kinase is TrkA. In some embodiments are provided such methods, wherein the tropomyosin-receptor-kinase is TrkB. In some embodiments are provided such methods, wherein the tropomyosin-receptor-kinase is TrkC. In some embodiments are provided such methods, wherein the at least one tropomyosin-receptor-kinase are TrkA and Trk B. In some embodiments are provided such methods, wherein the at least one tropomyosin-receptor-kinase are TrkA and Trk C. In some embodiments are provided such methods, wherein the at least one tropomyosin-receptor-kinase are TrkB and Trk C. In some embodiments are provided such methods, wherein the at least one tropomyosin-receptor-kinase are TrkA and Trk B and TrkC.

In some embodiments are provided methods for treating a cancer patient, comprising administering to the patient a therapeutically effective amount of at least one compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, in combination with at least one chemotherapeutic agent, wherein the cancer patient is neuroblastoma, and wherein the neuroblastoma is known to be tropomyosin-receptor-kinase positive prior to the administration. In some embodiments are provided such methods, wherein the compound administered to the patient in combination with at least one chemotherapeutic agent is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof. In some embodiments are provided such methods, wherein the at least one chemotherapeutic agent comprises at least one topoisomerase I inhibitor. In some embodiments are provided such methods, wherein the at least one chemotherapeutic agent comprises at least one alkylating agent. In some embodiments are provided such methods, wherein the at least one chemotherapeutic agent comprises at least one topoisomerase I inhibitor and at least one alkylating agent. In some embodiments are provided such methods, wherein the at least one topoisomerase I inhibitor is irinotecan. In some embodiments are provided such methods, wherein the at least one alkylating agent is temozolomide. In some embodiments are provided such methods, wherein the tropomyosin-receptor-kinase is at least one of TrkA, TrkB, and TrkC. In some embodiments are provided such methods, wherein the tropomyosin-receptor-kinase is TrkA. In some embodiments are provided such methods, wherein the tropomyosin-receptor-kinase is TrkB. In some embodiments are provided such methods, wherein the tropomyosin-receptor-kinase is TrkC. In some embodiments are provided such methods, wherein the at least one tropomyosin-receptor-kinase are TrkA and Trk B. In some embodiments are provided such methods, wherein the at least one tropomyosin-receptor-kinase are TrkA and Trk C. In some embodiments are provided such methods, wherein the at least one tropomyosin-receptor-kinase are TrkB and Trk C. In some embodiments are provided such methods, wherein the at least one tropomyosin-receptor-kinase are TrkA and Trk B and TrkC.

In some embodiments are provided methods for treating neuroblastoma in a patient, wherein prior to the treatment the neuroblastoma is known to possess at least one genetic alteration in at least one of NTRK1, NTRK2, and NTRK3, the method comprising administering to the patient a therapeutically effective amount of at least one compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, in combination with at least one chemotherapeutic agent. In some embodiments are provided such methods, wherein the compound administered to the patient in combination with at least one chemotherapeutic agent is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof. In some embodiments are provided such methods, wherein the at least one chemotherapeutic agent comprises at least one topoisomerase I inhibitor. In some embodiments are provided such methods, wherein the at least one chemotherapeutic agent comprises at least one alkylating agent. In some embodiments are provided such methods, wherein the at least one chemotherapeutic agent comprises at least one topoisomerase I inhibitor and at least one alkylating agent. In some embodiments are provided such methods, wherein the at least one topoisomerase I inhibitor is irinotecan. In some embodiments are provided such methods, wherein the at least one alkylating agent is temozolomide. In some embodiments are provided such methods, wherein the tropomyosin-receptor-kinase is at least one of TrkA, TrkB, and TrkC. In some embodiments are provided such methods, wherein the tropomyosin-receptor-kinase is TrkA. In some embodiments are provided such methods, wherein the tropomyosin-receptor-kinase is TrkB. In some embodiments are provided such methods, wherein the tropomyosin-receptor-kinase is TrkC. In some embodiments are provided such methods, wherein the at least one tropomyosin-receptor-kinase are TrkA and Trk B. In some embodiments are provided such methods, wherein the at least one tropomyosin-receptor-kinase are TrkA and Trk C. In some embodiments are provided such methods, wherein the at least one tropomyosin-receptor-kinase are TrkB and Trk C. In some embodiments are provided such methods, wherein the at least one tropomyosin-receptor-kinase are TrkA and Trk B and TrkC.

In some embodiments are provided methods for treating neuroblastoma in a patient, comprising (a) acquiring knowledge of the presence of at least one genetic alteration in at least one target gene in the neuroblastoma, wherein the at least one target gene is selected from NTRK1, NTRK2, and NTRK3; and (b) administering to the patient a therapeutically effective amount of at least one compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, in combination with at least one chemotherapeutic agent. In some embodiments are provided such methods, wherein the compound administered to the patient in combination with at least one chemotherapeutic agent is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof. In some embodiments are provided such methods, wherein the at least one chemotherapeutic agent comprises at least one topoisomerase I inhibitor. In some embodiments are provided such methods, wherein the at least one chemotherapeutic agent comprises at least one alkylating agent. In some embodiments are provided such methods, wherein the at least one chemotherapeutic agent comprises at least one topoisomerase I inhibitor and at least one alkylating agent. In some embodiments are provided such methods, wherein the at least one topoisomerase I inhibitor is irinotecan. In some embodiments are provided such methods, wherein the at least one alkylating agent is temozolomide. In some embodiments are provided such methods, wherein the tropomyosin-receptor-kinase is at least one of TrkA, TrkB, and TrkC. In some embodiments are provided such methods, wherein the tropomyosin-receptor-kinase is TrkA. In some embodiments are provided such methods, wherein the tropomyosin-receptor-kinase is TrkB. In some embodiments are provided such methods, wherein the tropomyosin-receptor-kinase is TrkC. In some embodiments are provided such methods, wherein the at least one tropomyosin-receptor-kinase are TrkA and Trk B. In some embodiments are provided such methods, wherein the at least one tropomyosin-receptor-kinase are TrkA and Trk C. In some embodiments are provided such methods, wherein the at least one tropomyosin-receptor-kinase are TrkB and Trk C. In some embodiments are provided such methods, wherein the at least one tropomyosin-receptor-kinase are TrkA and Trk B and TrkC.

In some embodiments are provided methods for treating neuroblastoma in a patient, the method comprising administering to the patient a therapeutically effective amount of at least one compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, in combination with at least one chemotherapeutic agent, and wherein the neuroblastoma is determined to express at least one tropomyosin-receptor-kinase. In some embodiments are provided such methods, wherein the compound administered to the patient in combination with at least one chemotherapeutic agent is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof. In some embodiments are provided such methods, wherein the at least one chemotherapeutic agent comprises at least one topoisomerase I inhibitor. In some embodiments are provided such methods, wherein the at least one chemotherapeutic agent comprises at least one alkylating agent. In some embodiments are provided such methods, wherein the at least one chemotherapeutic agent comprises at least one topoisomerase I inhibitor and at least one alkylating agent. In some embodiments are provided such methods, wherein the at least one topoisomerase I inhibitor is irinotecan. In some embodiments are provided such methods, wherein the at least one alkylating agent is temozolomide. In some embodiments are provided such methods, wherein the tropomyosin-receptor-kinase is at least one of TrkA, TrkB, and TrkC. In some embodiments are provided such methods, wherein the tropomyosin-receptor-kinase is TrkA. In some embodiments are provided such methods, wherein the tropomyosin-receptor-kinase is TrkB. In some embodiments are provided such methods, wherein the tropomyosin-receptor-kinase is TrkC.

In some embodiments are provided methods for treating neuroblastoma in a patient, comprising administering to the patient a therapeutically effective amount of at least one compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, in combination with at least one chemotherapeutic agent, and wherein the neuroblastoma is known to express at least one tropomyosin-receptor-kinase prior to the administration. In some embodiments are provided such methods, wherein the compound administered to the patient in combination with at least one chemotherapeutic agent is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof. In some embodiments are provided such methods, wherein the compound administered to the patient in combination with at least one chemotherapeutic agent is N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof. In some embodiments are provided such methods, wherein the at least one chemotherapeutic agent comprises at least one topoisomerase I inhibitor. In some embodiments are provided such methods, wherein the at least one chemotherapeutic agent comprises at least one alkylating agent. In some embodiments are provided such methods, wherein the at least one chemotherapeutic agent comprises at least one topoisomerase I inhibitor and at least one alkylating agent. In some embodiments are provided such methods, wherein the at least one topoisomerase I inhibitor is irinotecan. In some embodiments are provided such methods, wherein the at least one alkylating agent is temozolomide. In some embodiments are provided such methods, wherein the tropomyosin-receptor-kinase is at least one of TrkA, TrkB, and TrkC. In some embodiments are provided such methods, wherein the tropomyosin-receptor-kinase is TrkA. In some embodiments are provided such methods, wherein the tropomyosin-receptor-kinase is TrkB. In some embodiments are provided such methods, wherein the tropomyosin-receptor-kinase is TrkC. In some embodiments are provided such methods, wherein the at least one tropomyosin-receptor-kinase are TrkA and Trk B. In some embodiments are provided such methods, wherein the at least one tropomyosin-receptor-kinase are TrkA and Trk C. In some embodiments are provided such methods, wherein the at least one tropomyosin-receptor-kinase are TrkB and Trk C. In some embodiments are provided such methods, wherein the at least one tropomyosin-receptor-kinase are TrkA and Trk B and TrkC.

In any of the foregoing treatment embodiments, the chemotherapeutic agent can be administered simultaneously with the compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, or alternatively the chemotherapeutic agent can be administered before or after such compound.

In one embodiment, the chemotherapeutic agent and the compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, are administered on the same day. In another embodiment, the chemotherapeutic agent and the compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof are administered on alternative days or weeks. In one embodiment the chemotherapeutic agent is administered or not on alternating weeks and the compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof is administered daily or at least 1, 2, 3, 4, 5, 6, or 7 days per week. In some embodiments the patient is treated over a course of at least 1 week, 2, 3, 4, or 5 weeks, or 6, 7, 8, 9, 10, 12, 14, 16, or more weeks.

In some embodiments are provided pharmaceutical compositions, comprising (1) at least one compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, (2) at least one chemotherapeutic agent, and (3) at least one pharmaceutically acceptable excipient. In some embodiments are provided such pharmaceutical compositions comprising N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof, (2) at least one chemotherapeutic agent, and (3) at least one pharmaceutically acceptable excipient. In some embodiments are provided such pharmaceutical compositions wherein the compound is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof, (2) at least one chemotherapeutic agent, and (3) at least one pharmaceutically acceptable excipient. In some embodiments are provided such pharmaceutical compositions wherein the compound is N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, (2) at least one chemotherapeutic agent, and (3) at least one pharmaceutically acceptable excipient. In some embodiments are provided such pharmaceutical compositions, wherein the at least one chemotherapeutic agent comprises at least one topoisomerase I inhibitor. In some embodiments are provided such pharmaceutical compositions wherein said at least one chemotherapeutic agent comprises at least one topoisomerase I inhibitor and at least one alkylating agent. In some embodiments are provided such pharmaceutical compositions, wherein the at least one topoisomerase I inhibitor is irinotecan. In some embodiments are provided such pharmaceutical compositions, wherein the at least one chemotherapeutic agent comprises at least one alkylating agent. In some embodiments are provided such pharmaceutical compositions, wherein the at least one alkylating agent is temozolomide.

Some embodiments of the pharmaceutical compositions can comprise a physical admixture of the various ingredients in solid, liquid, or gelcap form. Other embodiments can comprise at least two separated ingredients in a single dosage unit or dosage form, such as, for example, a two- or three-layer tablet in which at least two active ingredients are located in separate layers or regions of the tablet, optionally separated by a third material, such as, for example, a sugar layer or other inert barrier to prevent contact between the first two ingredients. In other embodiments, two or more active ingredients are separately formulated into individual dosage units, which are then packaged together for ease of administration. One embodiment comprises a package containing a plurality of individual dosage units. This embodiment may, for example, comprise a blister package. In one embodiment of a blister package, multiple blister-packed dosage units are present on a single sheet, and those units that are to be administered together are packaged in the same or adjacent blisters of the blister pack. Alternatively, any other packaging can be used in which two active ingredients are packaged together for concurrent or sequential use.

In some embodiments are provided methods for treating neuroblastoma in a patient, the method comprising administering to said patient a therapeutically effective amount of a pharmaceutical composition, comprising (1) at least one compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, (2) at least one chemotherapeutic agent, and (3) at least one pharmaceutically acceptable excipient, and wherein said neuroblastoma is tropomyosin-receptor-kinase positive. In some embodiments are provided such methods, wherein said pharmaceutical composition comprises N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof, (2) at least one chemotherapeutic agent, and (3) at least one pharmaceutically acceptable excipient. In some embodiments are provided such methods, wherein said pharmaceutical composition comprises N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof, (2) at least one chemotherapeutic agent, and (3) at least one pharmaceutically acceptable excipient. In some embodiments are provided such methods, wherein said pharmaceutical composition comprises and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, (2) at least one chemotherapeutic agent, and (3) at least one pharmaceutically acceptable excipient. In some embodiments are provided such methods, wherein the at least one chemotherapeutic agent comprises at least one topoisomerase I inhibitor. In some embodiments are provided such methods, wherein the at least one chemotherapeutic agent comprises at least one alkylating agent. In some embodiments are provided such methods, wherein the at least one chemotherapeutic agent comprises at least one topoisomerase I inhibitor and at least one alkylating agent. In some embodiments are provided such methods, wherein the at least one topoisomerase I inhibitor is irinotecan. In some embodiments are provided such methods, wherein the at least one alkylating agent is temozolomide. In some embodiments are provided such methods, wherein the tropomyosin-receptor-kinase is at least one of TrkA, TrkB, and TrkC. In some embodiments are provided such methods, wherein the tropomyosin-receptor-kinase is TrkA. In some embodiments are provided such methods, wherein the tropomyosin-receptor-kinase is TrkB. In some embodiments are provided such methods, wherein the tropomyosin-receptor-kinase is TrkC. In some embodiments are provided such methods, wherein the at least one tropomyosin-receptor-kinase are TrkA and Trk B. In some embodiments are provided such methods, wherein the at least one tropomyosin-receptor-kinase are TrkA and Trk C. In some embodiments are provided such methods, wherein the at least one tropomyosin-receptor-kinase are TrkB and Trk C. In some embodiments are provided such methods, wherein the at least one tropomyosin-receptor-kinase are TrkA and Trk B and TrkC.

As used herein, the terms "comprising" and "including" are used in their open, non-limiting sense.

As used herein, the terms "treat," "treating," and "treatment" mean (i) preventing the disease or condition from occurring in a subject or patient which may be predisposed to the condition, such that the treatment constitutes prophylactic treatment for the pathologic condition; (ii) modulating or inhibiting the disease or condition, i.e., arresting its development; (iii) relieving the disease or condition, i.e., causing regression of the disease or condition; or (iv) relieving and/or alleviating the disease or condition or the symptoms resulting from the disease or condition. With regard to abnormal cell growth, such as cancer, these terms simply mean that the life expectancy of a subject or patient affected with abnormal cell growth will be increased or that one or more of the symptoms of the disease will be reduced. The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject or patient.

As used herein, the term "neuroblastoma" means a tumor of the postganglionic sympathetic nervous system.

As used herein, the term "therapeutically effective amount" means that amount of the compound or compounds being administered which will relieve to some extent one or more of the symptoms of the disorder being treated. In reference to the treatment of neuroblastoma, a therapeutically effective amount refers to that amount which has the effect of (1) reducing the size of a neuroblastoma tumor, (2) inhibiting (that is, slowing to some extent, preferably stopping) neuroblastoma tumor metastasis, (3) inhibiting to some extent (that is, slowing to some extent, preferably stopping) neuroblastoma tumor growth, and/or, (4) relieving to some extent (or, preferably, eliminating) one or more symptoms associated with the neuroblastoma.

As used herein, the term "N-[5-(3,5-difluorobenzyl)-1H-indazol-3-yl]-4-(piperazin-1-yl)-2-(tetrahydro-2H-pyran-4-ylamino) benzamide" means a compound having the chemical structure

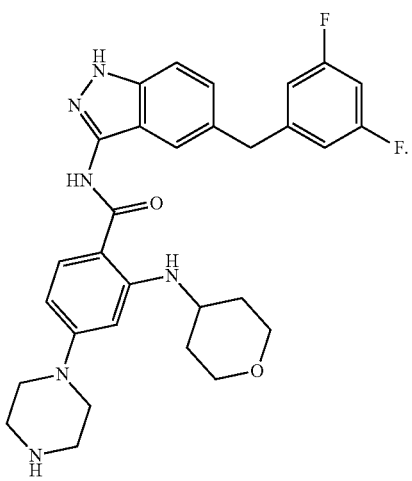 [SMILES: O=C(Nc1n[nH]c2ccc(Cc3cc(F)cc(F)c3)cc12)c1ccc(N2CCNCC2)cc1NC1CCOCC1]

As used herein, the term "N-[5-(3,5-difluorobenzyl)-1H-indazol-3-yl]-4-(4-methyl-piperazin-1-yl)-2-(tetrahydro-2H-pyran-4-ylamino) benzamide" means a compound having the chemical structure

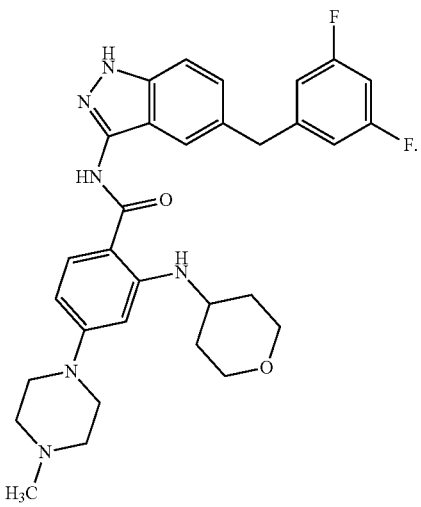 [SMILES: CN1CCN(c2ccc(C(=O)Nc3n[nH]c4ccc(Cc5cc(F)cc(F)c5)cc34)c(NC3CCOCC3)c2)CC1]

As used herein, the term "N-[5-(3,5-difluoro-benzenesulfonyl)-1H-indazol-3-yl]-2-((R)-2-methoxy-1-methyl-ethylamino)-4-(4-methyl-piperazin-1-yl) benzamide" means a compound having the chemical structure

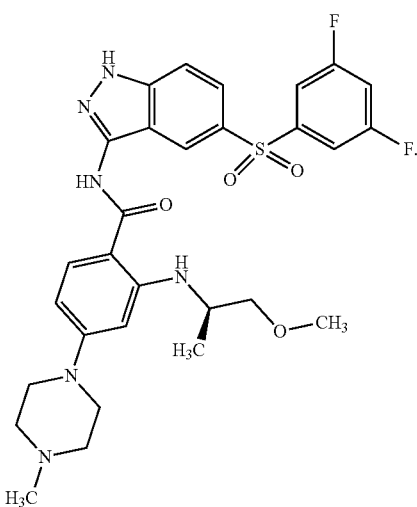 [SMILES: COC[C@@H](C)Nc1cc(N2CCN(C)CC2)ccc1C(=O)Nc1n[nH]c2ccc(S(=O)(=O)c3cc(F)cc(F)c3)cc12]

As used herein, the term "pharmaceutically acceptable salt" means a salt of a compound of the present disclosure that retains the biological effectiveness of the free acids and bases of the specified derivative and that is not biologically or otherwise undesirable. The term "pharmaceutically acceptable salt(s)," as used herein, unless otherwise indicated, includes salts of acidic or basic groups which may be present in the compounds disclosed herein.

As used herein, the term "chemotherapeutic agent" means a chemical agent that is used systemically for the treatment of cancer.

As used herein, the term "topoisomerase I inhibitor" means an agent that interferes with the action of the topoisomerase I enzyme.

As used herein, the term "irinotecan" means a compound having the chemical name (S)-4,11-diethyl-3,4,12,14-tetrahydro-4-hydroxy-3,14-dioxo1H-pyrany[3'4':6,7]-indolizino [1,2-b]quinolin-9-yl-[1,4'bipiperidine]-1'-carboxylate, and having the Chemical Abstracts registry number 100286-90-6.

As used herein, the term "temozolomide" means a compound having the chemical name 4-methyl-5-oxo-2,3,4,6,8-pentazabicyclo[4.3.0]nona-2,7,9-triene-9-carboxamide and having the Chemical Abstracts registry number 85622-93-1.

As used herein, the term "alkylating agent" means agents that are capable of forming highly reactive intermediate compounds that transfer alkyl groups to DNA thereby inhibiting the growth of cancer cells.

As used herein, the term "tropomyosin receptor kinase" means the family of tropomyosin receptor kinases (Trks) that are activated by peptide hormones of the neurotrophin family and include, but are not limited to, TrkA, TrkB, and TrkC.

As used herein, the term "TrkA" means wild-type tropomyosin receptor kinase A having the UniProt identifier NTRK1_HUMAN.

As used herein, the term "TrkB" means wild-type tropomyosin receptor kinase B having the UniProt identifier NTRK2_HUMAN.

As used herein, the term "TrkC" means wild-type tropomyosin receptor kinase C having the UniProt identifier NTRK3_HUMAN.

As used herein, the term "NTRK1" means the human gene that encodes for TrkA and having the ENSEMBL identifier ENSG00000198400.

As used herein, the term "NTRK2" means the human gene that encodes for TrkB and having the ENSEMBL identifier ENSG00000148053.

As used herein, the term "NTRK3" means the human gene that encodes for TrkC and having the ENSEMBL identifier ENSG00000140538.

As used herein, the term "tropomyosin receptor kinase positive" means that one or more cells from a neuroblastoma expresses one or more tropomyosin receptor kinase and/or contains one or more molecular alterations that results in an increase in activity or expression of one or more tropomyosin receptor kinase in said one or more cells compared to non-cancerous cells.

As used herein, the term "molecular alteration" means any variation in the genetic or protein sequence in or more cells of a patient as compared to the corresponding wild-type genes or proteins. Molecular alterations include, but are not limited to, genetic mutations, gene amplifications, splice variants, deletions, insertions/deletions, gene rearrangements, single-nucleotide variations (SNVs), insertions, and aberrant RNA/protein expression.

As used herein the terms "combination" and "in combination with" mean the administration of a compound disclosed herein together with an at least one additional pharmaceutical or medicinal agent (e.g., an anti-cancer agent), either sequentially or simultaneously. It includes dosing simultaneously, or within minutes or hours of each other, or on the same day, or on alternating days, or dosing the compound disclosed herein on a daily basis, or multiple days per week, or weekly basis, for example, while administering another compound such as a chemotherapeutic agent on the same day or alternating days or weeks or on a periodic basis during a time simultaneous therewith or concurrent therewith, or at least a part of the time during which the compound disclosed herein is dosed. For example, the compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof could be dosed every day or several days a week while the chemotherapeutic agent is dosed on alternating days or alternating weeks or other periods of time, such as every 1, 2, 3, 4, 5, 6, 7, 8, 9, 10, 11, 12, 13, 14 or more days.

Some embodiments include any of the methods described herein, wherein at least one of the compounds N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, are administered to a patient or individual having or suffering from neuroblastoma in an amount ranging from about 200 mg/m2 to about 1600 mg/m2, or from about 200 mg/m2 to about 1200 mg/m2, or from about 200 mg/m2 to about 1000 mg/m2, or from about 400 mg/m2 to about 1200 mg/m2, or from about 400 mg/m2 to about 1000 mg/m2, or from about 800 mg/m2 to about 1000 mg/m2, or from about 800 mg/m2 to about 1200 mg/m2, or from about 800 mg/m2 to about 1200 mg/m2, or from about 800 mg/m2 to about 1600 mg/m2. Some embodiments include any of the methods described herein, wherein at least one of the compounds described above are administered to said individual in an amount of about 200 mg/m2, about 300 mg/m2, about 400 mg/m2, about 500 mg/m2, about 600 mg/m2, about 700 mg/m2, about 800 mg/m2, about 900 mg/m2, about 1000 mg/m2, about 1100 mg/m2, about 1200 mg/m2, about 1300 mg/m2, about 1400 mg/m2, about 1500 mg/m2, about 1600 mg/m2, about 1700 mg/m2, about 1800 mg/m2, about 1900 mg/m2, or about 2000 mg/m2.

Some embodiments include any of the methods described herein, wherein at least one of the compounds N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, are administered to a patient or individual having or suffering from neuroblastoma in an amount ranging from about 0.01 mg/kg to about 100 mg/kg, or from about 0.02 mg/kg to about 50 mg/kg, or from about 0.05 mg/kg to about 25 mg/kg, or from about 0.1 mg/kg to about 20 mg/kg, or from about 0.2 mg/kg to about 10 mg/kg, or from about 0.5 mg/kg to about 5 mg/kg, or from about 1 mg/kg to about 2 mg/kg.

Some embodiments include any of the methods described herein wherein at least one of the compounds N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, are administered to an individual or patient having neuroblastoma in combination with at least one chemotherapeutic agent. In some embodiments are provided any of the methods described herein wherein the at least one chemotherapeutic agent is at least one topoisomerase I inhibitor. In some embodiments are provided any of the methods described herein wherein the least one topoisomerase I inhibitor is irinotecan. In some embodiments are provided any of the methods described herein wherein the at least one chemotherapeutic agent is at least one alkylating agent. In some embodiments are provided any of the methods described herein wherein the at least one alkylating agent is temozolomide.

In some embodiments are provided any of the methods described herein wherein at least one of the compounds described above is administered to an individual or patient having neuroblastoma in combination with at least one topoisomerase I inhibitor and at least one alkylating agent. In some embodiments are provided any of the methods described herein wherein the at least one topoisomerase I inhibitor is irinotecan. In some embodiments are provided any of the methods described herein the at least one alkylating agent is temozolomide. In some embodiments are provided any of the methods described herein wherein the at least one topoisomerase I inhibitor is irinotecan and the at least one alkylating agent is temozolomide.

Topoisomerase I inhibitors that may be used according to any of the methods disclosed herein include those known to those of ordinary skill in the art, including, but not limited to, irinotecan, topotecan, camptothecin and lamellarin D. Those of ordinary skill in the art will understand that with respect to topoisomersase I inhibitors that may be used according to any of the methods disclosed herein, the particular pharmaceutical formulation, the dosage, and the number of doses given per day to a mammal requiring such treatment, are all choices within the knowledge of one of ordinary skill in the art and can be determined without undue experimentation. For example, the appropriate dose of a topoisomerase I inhibitor given to an individual or patient according to any of the methods disclosed herein may be determined by reference to the FDA-approved labeling for any FDA-approved topoisomerase I inhibitor, such as irinotecan and topotecan.

Alkylating agents that may be used according to any of the methods disclosed herein include those known to those of ordinary skill in the art, including, but not limited to, nitrogen mustards such as mechlorethamine (nitrogen mustard), chlorambucil, cyclophosphamide, ifosfamide, and melphalan; nitrosoureas such as streptozocin, carmustine (BCNU), and lomustine; alkyl sulfonates such as busulfan; triazines such as dacarbazine (DTIC) and temozolomide; and ethylenimines such as thiotepa and altretamine (hexamethylmelamine). Those of ordinary skill in the art will understand that with respect to alkylating agents that may be used according to any of the methods disclosed herein, the particular pharmaceutical formulation, the dosage, and the number of doses given per day to a mammal requiring such treatment, are all choices within the knowledge of one of ordinary skill in the art and can be determined without undue experimentation. For example, the appropriate dose of an alkylating agent given to an individual or patient according to any of the methods disclosed herein may be determined by reference to the FDA-approved labeling for any FDA-approved alkylating agent, such as mechlorethamine, chlorambucil, cyclophosphamide, ifosfamide, melphalan, streptozocin, carmustine, lomustine, busulfan, dacarbazine, temozolomide, thiotepa, and altretamine.

The at least one chemotherapeutic agents may be administered to a patient in need thereof in an amount and in a dosing regimen known to those of ordinary skill in the art (for example, see J. Clinical Oncology, vol. 24, number 33, pp. 5271 to 5276 (2006). For example, patients with refractory or relapsed neuroblastoma may receive one or more 5-day courses of irinotecan at a dose of about 50 mg per meters squared per day infused intravenously over one hour (resulting in a dose of about 250 mg per meters squared per course) plus temozolomide in a dose of about 150 mg meters squared per day (resulting in a dose of about 750 mg per meters squared per course) taken orally. Such treatment courses may be started about every 3 to 4 weeks when the pretreatment platelet counts of the patients are, for example, more than about 30,000 per microliter (untransfused). Patients may also be treated with granulocyte colony-stimulating factor when the absolute neutrophil count decreased to less than 1,000 per microliter. Patients may also be dosed with a compound such as loperamide if they experience diarrhea.

Disease status of patients may be assessed by computed tomography (CT; or magnetic resonance imaging (MRI)), [123Iodine] metaiodobenzylguanidine scan, urine catecholamines, and bilateral BM biopsies and aspirates. These tests may generally be carried out after every two to three courses of treatment. The International Neuroblastoma Response Criteria (INRC) may be used to determine the effect of treatment on patients: complete response (CR), no evidence of neuroblastoma; very good partial response, volume of primary mass reduced by more than 90%, no evidence of distant neuroblastoma (including normal metaiodobenzylguanidine scans) except for skeletal residua, catecholamines normal; partial response (PR), more than 50% decrease in measurable disease and ≤1 positive neuroblastoma site; mixed response, more than 50% decrease of any lesion with less than 50% decrease in any other; no response, less than 50% decrease but less than 25% increase in any lesion; and progressive disease (PD), new lesion or more than 25% increase in an existing lesion.

In some embodiments are provided any of the methods disclosed herein wherein an individual or patient having or suffering from neuroblastoma is tested to determine whether one or more cells comprising the neuroblastoma contain at least one relevant molecular alteration. Such relevant molecular alterations include, but are not limited to, molecular alterations with respect to Trk. Such molecular alterations to Trk can include, but are not limited to, molecular alterations involving one or more of TrkA, TrkB, TrkC proteins, NTRK1, NTRK2, and NTRK3 genes or gene products. Such molecular alterations may include, but are not limited to, genetic mutations, gene amplifications, splice variants, deletions, insertions/deletions, gene rearrangements, single-nucleotide variations (SNVs), insertions, and aberrant RNA/protein expression.

Transcript accumulation levels, genomic locus screening methods, and protein kinase activity assays for at least one of TrkA, TrkB, TrkC may be performed using methods known to those of ordinary skill in the art. For example, kinase assays may be performed by providing a substrate to a protein extract comprising at least one of TrkA, TrkB, TrkC. Further, TrkA, TrkB, or TrkC locus sequencing may be performed using, for example, whole genome shotgun sequencing, or targeted sequencing or re-sequencing of the TrkA, TrkB, or TrkC locus, for example through targeted amplification of the locus or a region spanning the locus wholly or in part, using PCR techniques known to one of ordinary skill in the art and primers generated through means known to one of ordinary skill in the art, followed by sequencing of any generated amplicons. Molecular alterations may also be detected by those of ordinary skill in the art using one or more of next generation sequencing (NGS), quantitative reverse-transcription polymerase chain reaction DNA amplification reactions (qPCR), fluorescence in situ hybridization (FISH), and/or immunohistochemistry (IHC).

A DNA-based test may be used by one of ordinary skill in the art to detect molecular alterations such as copy number variations, single-nucleotide variations, insertions, deletions, and gene rearrangements. An RNA-based test may be used by one of ordinary skill in the art to detect the same variations described for DNA and additionally, over expression, under expression (up to and including complete loss of expression) or misexpression of at least one of TrkA, TrkB, or TrkC. Protein-based tests may be used by one of ordinary skill in the art to measure the over expression, under expression (through and including complete loss of expression), misexpression, constitutive phosphorylation, constitutive dephosphorylation, misphosphorylation, increase, decrease (through and including complete loss) or altered activity pattern of at least one of TrkA, TrkB, and TrkC.

Some embodiments relate to the use of any of the compounds as described herein, or a pharmaceutically acceptable salt thereof, in the manufacture of a medicament for the treatment of abnormal cell growth in a mammal. The present disclosure further relates to the use of any of the compounds as described herein, or a pharmaceutically acceptable salt thereof, in the manufacture of a medicament for the treatment of abnormal cell growth in a mammal wherein the abnormal cell growth is cancerous or non-cancerous. In some embodiments, the abnormal cell growth is cancerous. In another embodiment, the abnormal cell growth is non-cancerous.

Some embodiments relate to any of the compounds described herein, or pharmaceutically acceptable salts thereof, for use as a medicament. Some embodiments relate to the use of any of the compounds described above, or pharmaceutically acceptable salts thereof, for the manufacture of a medicament for the treatment of abnormal cell growth.

As used herein "cancer" refers to any malignant and/or invasive growth or tumor caused by abnormal cell growth. As used herein "cancer" refers to solid tumors named for the type of cells that form them, cancer of blood, bone marrow, or the lymphatic system. Examples of solid tumors include but are not limited to sarcomas and carcinomas. Examples of cancers of the blood include but are not limited to leukemias, lymphomas and myeloma. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one.

Some embodiments relate to compositions comprising a compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof (e.g., pharmaceutical compositions). Accordingly, in some embodiments, the disclosure relates to a pharmaceutical composition comprising a compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt, a pharmaceutically acceptable carrier and, optionally, at least one additional medicinal or pharmaceutical agent. In some embodiments, the at least one additional medicinal or pharmaceutical agent is an anti-cancer agent as described below. In some embodiments, the compound is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof. In some embodiments, the compound is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof. In some embodiments, the compound is N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof. In some embodiments, the compound is at least two of N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof.

The pharmaceutically acceptable carrier may comprise a conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

In some embodiments, the composition comprises a therapeutically effective amount of a compound as disclosed herein and a pharmaceutically acceptable carrier.

The compounds of the present disclosure may be formulated into pharmaceutical compositions as described below in any pharmaceutical form recognizable to the skilled artisan as being suitable. Pharmaceutical compositions of the disclosure comprise a therapeutically effective amount of at least one compound disclosed herein and an inert, pharmaceutically acceptable carrier or diluent.

To treat or prevent diseases or conditions mediated by ALK, ROS1, TrkA, TrkB, or TrkC, or a combination thereof, a pharmaceutical composition of the disclosure is administered in a suitable formulation prepared by combining a therapeutically effective amount (i.e., a ALK, ROS1, TrkA, TrkB, or TrkC modulating, regulating, or inhibiting amount effective to achieve therapeutic efficacy) of at least one compound of the present disclosure (as an active ingredient) with one or more pharmaceutically suitable carriers, which may be selected, for example, from diluents, excipients and auxiliaries that facilitate processing of the active compounds into the final pharmaceutical preparations.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g. parenteral or oral administration.

To obtain a stable water-soluble dose form, a salt of a compound of the present disclosure may be dissolved in an aqueous solution of an organic or inorganic acid, such as a 0.3 M solution of succinic acid or citric acid. If a soluble salt form is not available, the agent may be dissolved in a suitable co-solvent or combinations of co-solvents. Examples of suitable co-solvents include alcohol, propylene glycol, polyethylene glycol 300, polysorbate 80, glycerin and the like in concentrations ranging from 0 to 60% of the total volume. In an exemplary embodiment, a compound of the present disclosure is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration selected. For injection, the agents of the compounds of the present disclosure may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers known in the art. Such carriers enable the compounds of the disclosure to be formulated as tablets, pills, dragees, capsules, liquids, gels, syrups, slurries, suspensions and the like, for oral ingestion by a subject to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g. sterile pyrogen-free water, before use.

In addition to the formulations described above, the compounds of the present disclosure may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt. A pharmaceutical carrier for hydrophobic compounds is a co-solvent system comprising benzyl alcohol, a non-polar surfactant, a water-miscible organic polymer, and an aqueous phase. The co-solvent system may be a VPD co-solvent system. VPD is a solution of 3% w/v benzyl alcohol, 8% w/v of the non-polar surfactant polysorbate 80, and 65% w/v polyethylene glycol 300, made up to volume in absolute ethanol. The VPD co-solvent system (VPD: 5 W) contains VPD diluted 1:1 with a 5% dextrose in water solution. This co-solvent system dissolves hydrophobic compounds well, and itself produces low toxicity upon systemic administration. The proportions of a co-solvent system may be suitably varied without destroying its solubility and toxicity characteristics. Furthermore, the identity of the co-solvent components may be varied: for example, other low-toxicity non-polar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol®, Transcutol® and the like may be used.

Further, the pharmaceutical composition may be incorporated into a skin patch for delivery of the drug directly onto the skin.

It will be appreciated that the actual dosages of the agents of this disclosure will vary according to the particular agent being used, the particular composition formulated, the mode of administration, and the particular site, host, and disease being treated. Those skilled in the art using conventional dosage-determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals.

Furthermore, the pharmaceutically acceptable formulations of the present disclosure may contain a compound or compounds of the present disclosure, or a salt or solvate thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg. Furthermore, the pharmaceutically acceptable formulations of the present disclosure may contain a compound of the present disclosure, or a salt or solvate thereof, in an amount of about 50 mg, about 100 mg, about 150 mg, about 200 mg, about 250 mg, about 300 mg, about 350 mg, about 400 mg, about 450 mg, or about 500 mg.

Additionally, the pharmaceutically acceptable formulations of the present disclosure may contain a compound of the present disclosure, or a salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

The compounds disclosed herein, or salts or solvates thereof, may be administered to a mammal suffering from abnormal cell growth, such as a human, either alone or as part of a pharmaceutically acceptable formulation, once a week, once a day, twice a day, three times a day, or four times a day, or even more frequently.

Those of ordinary skill in the art will understand that with respect to the compounds of the present disclosure, the particular pharmaceutical formulation, the dosage, and the number of doses given per day to a mammal requiring such treatment, are all choices within the knowledge of one of ordinary skill in the art and can be determined without undue experimentation.

Administration of the compounds disclosed herein may be effected by any method that enables delivery of the compounds to the site of action. These methods include oral routes, intraduodenal routes, parenteral injection (including intravenous, subcutaneous, intramuscular, intravascular or infusion), topical, and rectal administration. Bolus doses can be used, or infusions over a period of 1, 2, 3, 4, 5, 10, 15, 20, 30, 60, 90, 120 or more minutes, or any intermediate time period can also be used, as can infusions lasting 3, 4, 5, 6, 7, 8, 9, 10, 12, 14 16, 20, 24 or more hours or lasting for 1-7 days or more. Infusions can be administered by drip, continuous infusion, infusion pump, metering pump, depot formulation, or any other suitable means.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the disclosure are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present disclosure.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present disclosure encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

Preparation of formulation and dosage forms comprising N-[5-(3,5-difluorobenzyl)-1H-indazol-3-yl]-4-(4-methyl-piperazin-1-yl)-2-(tetrahydro-2H-pyran-4-ylamino) benzamide.

Hard gelatin capsules comprising 50 mg, 100 mg, and 200 mg of N-[5-(3,5-difluorobenzyl)-1H-indazol-3-yl]-4-(4-methyl-piperazin-1-yl)-2-(tetrahydro-2H-pyran-4-ylamino) benzamide were prepared as follows.

The required amounts of active ingredient and excipients are weighed into the warehouse dispensing area. The weight of N-[5-(3,5-difluorobenzyl)-1H-indazol-3-yl]-4-(4-methyl-piperazin-1-yl)-2-(tetrahydro-2H-pyran-4-ylamino) benzamide and the mannitol are adjusted according to the active desired potency of the dosage form. (1) Manually pre-mix N-[5-(3,5-difluorobenzyl)-1H-indazol-3-yl]-4-(4-methyl-piperazin-1-yl)-2-(tetrahydro-2H-pyran-4-ylamino) benzamide and colloidal silicon dioxide into a polyethylene (PE) bag. (2) The resulting mixture from step 1 is passed through a 0.500 mm screen size sieve, along with a portion of the pregelatinized starch and mannitol and the resulting materials are collected in a blender. (3) The resulting mixture from step 2 is further mixed for about 20 minutes at 20-25 rpm. (4) The pregelatinized starch and magnesium stearate and are pre-mixed together and are passed through a 0.500 mm screen size sieve. (5) The material from step 4 are mixed together with the materials from step 3 and mixed for about 20 minutes at 20-25 rpm. (6) The blend resulting from step 5 is filled into hard gelatin capsules using an automatic capsule filling machine. Representative formulations of capsules comprising 50 mg, 100 mg or 200 mg of N-[5-(3,5-difluorobenzyl)-1H-indazol-3-yl]-4-(4-methyl-piperazin-1-yl)-2-(tetrahydro-2H-pyran-4-ylamino) benzamide are shown below.

| 50 mg capsule representative batch formulation | | | |
|---|---|---|---|
| Components | Function | Batch formula 50 mg (6,000 capsules) | Amount per capsule 50 mg |
| N-[5-(3,5-difluorobenzyl)-1H-indazol-3-yl]-4-(4-methyl-piperazin-1-yl)-2-(tetrahydro-2H-pyran-4-ylamino) benzamide | Active ingredient | 300 g | 50 mg |
| Mannitol | Filler | 255.00 g | 42.50 mg |
| Pregelatinized starch | Filler | 102.75 g | 17.125 mg |
| Colloidal silicon dioxide | Glidant | 10.50 g | 1.750 mg |
| Magnesium stearate | Lubricant | 6.75 g | 1.125 mg |
| Total | | 675.00 g | 112.50 mg |

| 100 mg capsule representative batch formulation | | | |
|---|---|---|---|
| Components | Function | Batch formula 100 mg (3,600 capsules) | Amount per capsule 100 mg |
| N-[5-(3,5-difluorobenzyl)-1H-indazol-3-yl]-4-(4-methyl-piperazin-1-yl)-2-(tetrahydro-2H-pyran-4-ylamino) benzamide | Active ingredient | 360.0 g | 100.00 mg |
| Mannitol | Filler | 306.00 g | 85.00 mg |
| Pregelatinized starch | Filler | 123.30 g | 34.25 mg |
| Colloidal silicon dioxide | Glidant | 12.60 g | 3.50 mg |
| Magnesium stearate | Lubricant | 8.10 g | 2.25 mg |
| Total | | 810.00 g | 225.00 mg |

| 200 mg capsule representative batch formulation | | | |
|---|---|---|---|
| Components | Function | Batch formula 200 mg (4,100 capsules) | Amount per capsule 200 mg |
| N-[5-(3,5-difluorobenzyl)-1H-indazol-3-yl]-4-(4-methyl-piperazin-1-yl)-2-(tetrahydro-2H-pyran-4-ylamino) benzamide | Active ingredient | 820.00 g | 200.00 mg |
| Mannitol | Filler | 697.00 g | 170.00 mg |
| Pregelatinized starch | Filler | 280.85 g | 68.50 mg |
| Colloidal silicon dioxide | Glidant | 28.70 g | 7.00 mg |
| Magnesium stearate | Lubricant | 18.45 g | 4.50 mg |
| Total | | 1845.00 g | 450.00 mg |

Representative formulations of capsules comprising 50 mg, 100 mg or 200 mg of N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide or N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt of either of them, may be prepared by one having ordinary skill in the art according to the methods and procedures described above.

Addition of N-[5-(3,5-difluorobenzyl)-1H-indazol-3-yl]-4-(4-methyl-piperazin-1-yl)-2-(tetrahydro-2H-pyran-4-ylamino) benzamide to a combination of temozolomide and irinotecan in models of neuroblastoma (NB)

NB is one of the most common and deadly solid tumors of childhood. The Trk family of neurotrophin receptors plays an important role in clinical behavior of NBs. Overexpression of TrkB and its ligand brain-derived neurotrophic factor (BDNF) is associated with poor prognosis.

N-[5-(3,5-difluorobenzyl)-1H-indazol-3-yl]-4-(4-methyl-piperazin-1-yl)-2-(tetrahydro-2H-pyran-4-ylamino) benzamide_was dissolved in DMSO to obtain stocks for in vitro studies. For in vivo xenograft experiments, N-[5-(3,5-difluorobenzyl)-1H-indazol-3-yl]-4-(4-methyl-piperazin-1-yl)-2-(tetrahydro-2H-pyran-4-ylamino) benzamide was reconstituted in 0.5% methyl cellulose (Sigma-Aldrich, viscosity 400 cP, 2% in $H_2O$) containing 1% Tween 80 at a final dosing volume of 10 mL per kg. Prior to dosing, the formulation was stirred at room temperature for 30 min, and then sonicated in a water bath sonicator for 20 min. The formulation was made fresh every week. For the in vivo study, the animals were dosed with the formulation of N-[5-(3,5-difluorobenzyl)-1H-indazol-3-yl]-4-(4-methyl-piperazin-1-yl)-2-(tetrahydro-2H-pyran-4-ylamino) benzamide twice a day (BID) for 7 days per week at a dose of 60 mg per kg.

Temozolomide (Temodar, Teva, 20 mg per capsule) was reconstituted in a saline solution at a concentration of 1 mg/mL. For the in vivo study, animals were dosed orally with the formulation comprising temozolomide once per day at a dose of 7.5 mg per kg Monday through Friday of each week (except for the groups that received the compound every other week). Irinotecan (Camptosar, Novaplus, 20 mg per mL) was diluted in a saline solution and animals were dosed orally at a dose of 0.63 mg per kg Monday through Friday of each week.

Xenograft studies were performed using SH-SY5Y cells stably transfected with TrkB. Cells were grown in RPMI-1640 medium containing 10% fetal bovine serum and maintained in 150 $cm^3$ Costar culture flasks in a humidified atmosphere of 95% air and 5% $CO_2$. Cells were harvested using 0.2% tetra sodium EDTA in phosphate buffered saline (PBS).

Six-week-old athymic nu/nu mice were obtained from Jackson Laboratories. Mice were maintained at five per cage under humidity- and temperature-controlled conditions in a light/dark cycle that was set at 12-hour intervals. The Institutional Animal Care Committee of the Joseph Stokes, Jr. Research Institute at CHOP approved the animal studies described herein.

In Vitro Experiments

Sulphorhodamine B (SRB) assays were performed to determine the effect of N-[5-(3,5-difluorobenzyl)-1H-indazol-3-yl]-4-(4-methyl-piperazin-1-yl)-2-(tetrahydro-2H-pyran-4-ylamino) benzamide as a single agent and in combination with irinotecan and temozolomide on the survival and growth of the TrkB-expressing neuroblastoma cells. $5 \times 10^3$ cells per well were plated in 96 well plates and exposed to drug at different concentrations (1 nM, 5 nM, 10 nM, 20 nM, 30 nM, 50 nM and 100 nM of N-[5-(3,5-difluorobenzyl)-1H-indazol-3-yl]-4-(4-methyl-piperazin-1-yl)-2-(tetrahydro-2H-pyran-4-ylamino) benzamide, 1.5 μM irinotecan and 50 μM temozolomide, respectively) for one hour followed by addition of 100 ng per mL of brain-derived neurotrophic factor (BDNF). Cells from the plates were harvested at 24 hours, 48 hours, and 72 hours following addition of compound. The plates were processed via standard sulforhodamine B (SRB) assay protocols known to those of ordinary skill in the art (for example, see Vichai et al., *Nature Protocols* 1, pp. 1112-1116 (2006)). All in vitro experiments were performed in triplicate and repeated at least three times.

The use of N-[5-(3,5-difluorobenzyl)-1H-indazol-3-yl]-4-(4-methyl-piperazin-1-yl)-2-(tetrahydro-2H-pyran-4-ylamino) benzamide as a single agent significantly inhibited growth of TrkB-expressing NB cells in vitro. The use of N-[5-(3,5-difluorobenzyl)-1H-indazol-3-yl]-4-(4-methyl-piperazin-1-yl)-2-(tetrahydro-2H-pyran-4-ylamino) benzamide in combination with irinotecan and temozolomide demonstrated enhanced inhibition of the growth of TrkB-expressing NB cells in vitro.

In Vivo Experiments

For in vivo xenograft studies, six-week-old athymic nu/nu mice were injected subcutaneously in the flank with $1 \times 10^7$ SY5Y-TrkB cells in 0.1 ml of Matrigel (BD Bioscience, Palo Alto, Calif.). Tumors were measured 2 times per week in 3 dimensions, and the volume calculated as follows: [(0.523× L×W×W)/1000]. Body weights of the mice were obtained every week and the dose of the tested compounds were adjusted accordingly. Treatment with N-[5-(3,5-difluorobenzyl)-1H-indazol-3-yl]-4-(4-methyl-piperazin-1-yl)-2-(tetrahydro-2H-pyran-4-ylamino) benzamide, irinotecan and temozolmide was started about 15-17 days after tumor inoculation when the average tumor size was about 0.2 $cm^3$. Mice were sacrificed when tumor volume reached about 3 $cm^3$. Tumors were harvested and flash frozen on dry ice for analysis of protein expression using Western blot analysis that was performed using methods known to those of ordinary skill in the art. Plasma samples were obtained from the animals at various time points post-dosing for the purpose of pharmacokinetic (PK) and pharmacodynamic (PD) analyses.

Animals were treated with one of 6 different treatment regimens:

(1) control (treated with vehicle alone);

(2) a combination of irinotecan and temozolomide (both oral, once per day, 5 times per week on weeks 1, 3, and 5) alternating with treatment with N-[5-(3,5-difluorobenzyl)-1H-indazol-3-yl]-4-(4-methyl-piperazin-1-yl)-2-(tetrahydro-2H-pyran-4-ylamino) benzamide (oral, 60 mg per kg, twice a day, 7 times per week on weeks 2, 4, and 6);

(3) irinotecan and temozolomide (both oral, once per day, 5 times per week);

(4) N-[5-(3,5-difluorobenzyl)-1H-indazol-3-yl]-4-(4-methyl-piperazin-1-yl)-2-(tetrahydro-2H-pyran-4-ylamino) benzamide alone (oral, 60 mg per kg, twice per day, 7 times per week);

(5) N-[5-(3,5-difluorobenzyl)-1H-indazol-3-yl]-4-(4-methyl-piperazin-1-yl)-2-(tetrahydro-2H-pyran-4-ylamino) benzamide (oral, 60 mg per kg, twice per day, 7 times per week throughout the study) plus irinotecan and temozolomide (both oral, once per day, 5 times per week on weeks 1, 3 and 5); and (6) N-[5-(3,5-difluorobenzyl)-1H-indazol-3-yl]-4-(4-methyl-piperazin-1-yl)-2-(tetrahydro-2H-pyran-4-ylamino) benzamide (oral, 60 mg per kg, twice per day, 7 times per week throughout the study), plus irinotecan and temozolomide (both oral, once per day, 5 times per week throughout the study).

A linear mixed effects model was used to test the difference in the rate of tumor volume changing over time between different treatment groups. The model included group, day, and group-by-day interaction as fixed effects, and included a random intercept and a random slope for each test animal (mouse). A significant group-by-day interaction would suggest that the tumor volume changes at different rates for the two comparison groups. The model used the control group as the reference group and created separate group indicators and interaction terms for other groups. Appropriate contrast statements were created to compare the two groups other than control group (e.g. group 2 that was treated with N-[5-(3,5-difluorobenzyl)-1H-indazol-3-yl]-4-(4-methyl-piperazin-1-yl)-2-(tetrahydro-2H-pyran-4-ylamino) benzamide alone versus Group 4 that was treated with N-[5-(3,5-difluorobenzyl)-1H-indazol-3-yl]-4-(4-methyl-piperazin-1-yl)-2-(tetrahydro-2H-pyran-4-ylamino) benzamide plus irinotecan and temozolomide).

The tumor growth in the study animals did not appear to be linear in the studies and became approximately linear after log transformation. So we first log transformed the data and then applied linear mixed effects model described above.

For the studies, the results are reflective of the on-treatment period as there was too little data for with respect to the off-treatment period.

Single agent therapy with N-[5-(3,5-difluorobenzyl)-1H-indazol-3-yl]-4-(4-methyl-piperazin-1-yl)-2-(tetrahydro-2H-pyran-4-ylamino) benzamide resulted in significant tumor growth inhibition compared to control animals [p<0.0001 for event-free survival (EFS)]. The addition of N-[5-(3,5-difluorobenzyl)-1H-indazol-3-yl]-4-(4-methyl-piperazin-1-yl)-2-(tetrahydro-2H-pyran-4-ylamino) benzamide to a combination of irinotecan and temozolomide also significantly improved the EFS of treated animals compared to animals treated with vehicle (control) or a combination of irinotecan and temozolomide without N-[5-(3,5-difluorobenzyl)-1H-indazol-3-yl]-4-(4-methyl-piperazin-1-yl)-2-(tetrahydro-2H-pyran-4-ylamino) benzamide (p<0.0001 for combination vs. vehicle (control); p=0.0012 for combination of N-[5-(3,5-difluorobenzyl)-1H-indazol-3-yl]-4-(4-methyl-piperazin-1-yl)-2-(tetrahydro-2H-pyran-4-ylamino) benzamide with irinotecan and temozolomide vs. temozolomide and irinotecan without N-[5-(3,5-difluorobenzyl)-1H-indazol-3-yl]-4-(4-methyl-piperazin-1-yl)-2-(tetrahydro-2H-pyran-4-ylamino) benzamide).

FIG. 1 shows the growth of tumors on animals treated with:

(1) Group 1: control (treated with vehicle alone) (solid line with diamonds);

(2) Group 5: a combination of irinotecan and temozolomide (both oral, once per day, 5 times per week on weeks 1, 3, and 5) alternating with treating with N-[5-(3,5-difluorobenzyl)-1H-indazol-3-yl]-4-(4-methyl-piperazin-1-yl)-2-(tetrahydro-2H-pyran-4-ylamino) benzamide (oral, 60 mg per kg, twice a day, 7 times per week on weeks 2, 4, and 6) (dotted line with solid squares; solid bars represent period of dosing with N-[5-(3,5-difluorobenzyl)-1H-indazol-3-yl]-4-(4-methyl-piperazin-1-yl)-2-(tetrahydro-2H-pyran-4-ylamino) benzamide on weeks 2, 4 and 6);

(3) Group 3: irinotecan and temozolomide (both oral, once per day, 5 times per week) (solid line with solid circles);

(4) Group 2: N-[5-(3,5-difluorobenzyl)-1H-indazol-3-yl]-4-(4-methyl-piperazin-1-yl)-2-(tetrahydro-2H-pyran-4-ylamino) benzamide alone (oral, 60 mg per kg, twice per day, 7 times per week) (solid line with triangles);

(5) Group 6: N-[5-(3,5-difluorobenzyl)-1H-indazol-3-yl]-4-(4-methyl-piperazin-1-yl)-2-(tetrahydro-2H-pyran-4-ylamino) benzamide (oral, 60 mg per kg, twice per day, 7 times per week throughout the study) plus irinotecan and temozolomide (both oral, once per day, 5 times per week on weeks 1, 3 and 5) (dotted line with open squares); and (6) Group 4: N-[5-(3,5-difluorobenzyl)-1H-indazol-3-yl]-4-(4-methyl-piperazin-1-yl)-2-(tetrahydro-2H-pyran-4-ylamino) benzamide (oral, 60 mg per kg, twice per day, 7 times per week throughout the study), plus irinotecan and temozolomide (both oral, once per day, 5 times per week throughout the study) (solid line with solid squares).

Figure 2:
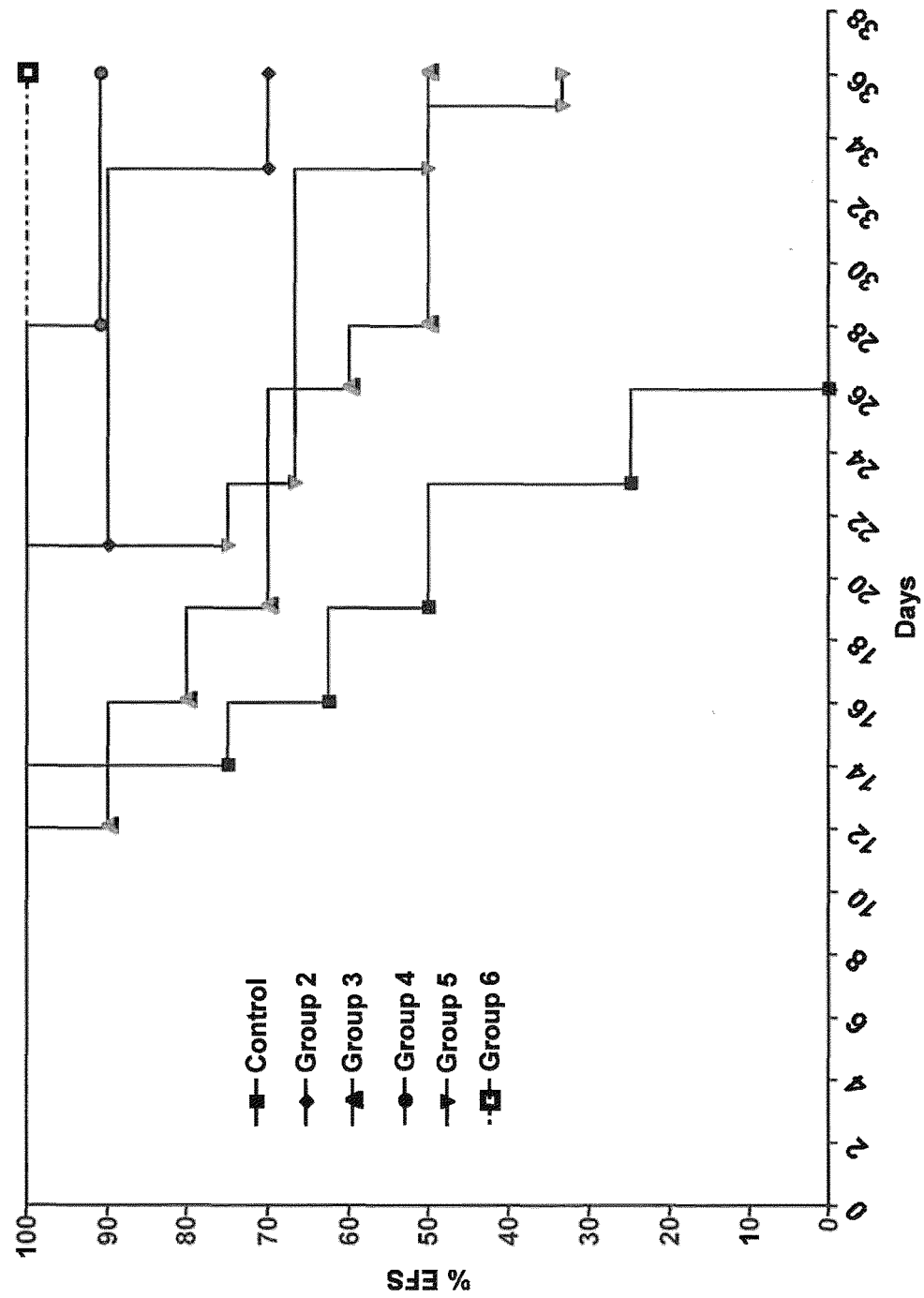
FIG. 2 shows the percentage of event-free survival (EFS) for animals treated with (1) control (treated with vehicle) (solid line with solid squares and labeled as Control); (2) Group 3: a combination of irinotecan and temozolomide (both oral, once per day, 5 times per week) (solid line with solid triangles); (3) Group 5: a combination of irinotecan and temozolomide (both oral, once per day, 5 times per week on weeks 1, 3, and 5) alternating with treating with N-[5-(3,5-difluorobenzyl)-1H-indazol-3-yl]-4-(4-methyl-piperazin-1-yl)-2-(tetrahydro-2H-pyran-4-ylamino) benzamide (oral, 60 mg per kg, twice a day, 7 times per week on weeks 2, 4, and 6) (solid line with upside-down triangles); (4) Group 2: N-[5-(3,5-difluorobenzyl)-1H-indazol-3-yl]-4-(4-methyl-piperazin-1-yl)-2-(tetrahydro-2H-pyran-4-ylamino) benzamide alone (oral, 60 mg per kg, twice per day, 7 times per week) (solid line with solid diamonds); (5) Group 4: N-[5-(3,5-difluorobenzyl)-1H-indazol-3-yl]-4-(4-methyl-piperazin-1-yl)-2-(tetrahydro-2H-pyran-4-ylamino) benzamide (oral, 60 mg per kg, twice per day, 7 times per week throughout the study), irinotecan and temozolomide (both oral, once per day, 5 times per week throughout the study) (solid line with solid circles); and (6) Group 6: N-[5-(3,5-difluorobenzyl)-1H-indazol-3-yl]-4-(4-methyl-piperazin-1-yl)-2-(tetrahydro-2H-pyran-4-ylamino) benzamide (oral, 60 mg per kg, twice per day, 7 times per week throughout the study), irinotecan and temozolomide (both oral, once per day, 5 times per week on weeks 1, 3 and 5) (dotted line with open squares).

FIG. 2 shows the percentage of event-free survival (EFS) for animals treated with:

(1) Control: control (treated with vehicle) (solid line with solid squares and labeled as Control);

(2) Group 3: a combination of irinotecan and temozolomide (both oral, once per day, 5 times per week) (solid line with solid triangles);

(3) Group 5: a combination of irinotecan and temozolomide (both oral, once per day, 5 times per week on weeks 1, 3, and 5) alternating with treating with N-[5-(3,5-difluorobenzyl)-1H-indazol-3-yl]-4-(4-methyl-piperazin-1-yl)-2-(tetrahydro-2H-pyran-4-ylamino) benzamide (oral, 60 mg per kg, twice a day, 7 times per week on weeks 2, 4, and 6) (solid line with upside-down triangles);

(4) Group 2: N-[5-(3,5-difluorobenzyl)-1H-indazol-3-yl]-4-(4-methyl-piperazin-1-yl)-2-(tetrahydro-2H-pyran-4-ylamino) benzamide alone (oral, 60 mg per kg, twice per day, 7 times per week) (solid line with solid diamonds);

(5) Group 4: N-[5-(3,5-difluorobenzyl)-1H-indazol-3-yl]-4-(4-methyl-piperazin-1-yl)-2-(tetrahydro-2H-pyran-4-ylamino) benzamide (oral, 60 mg per kg, twice per day, 7 times per week throughout the study), irinotecan and temozolomide (both oral, once per day, 5 times per week throughout the study) (solid line with solid circles); and (6) Group 6: N-[5-(3,5-difluorobenzyl)-1H-indazol-3-yl]-4-(4-methyl-piperazin-1-yl)-2-(tetrahydro-2H-pyran-4-ylamino) benzamide (oral, 60 mg per kg, twice per day, 7 times per week throughout the study), irinotecan and temozolomide (both oral, once per day, 5 times per week on weeks 1, 3 and 5) (dotted line with open squares).

Event free survival (EFS) curves were estimated using Kaplan-Meier method and compared using log-rank test. Event includes death and sacrifice mice due to tumor burden. Estimated slopes from linear mixed effects model:

| | Group | |
|---|---|---|
| | Control | Group 2 |
| slope | 0.1891 | 0.0973 |

P values for comparisons of slopes between two groups: <0.0001

Figure 3:
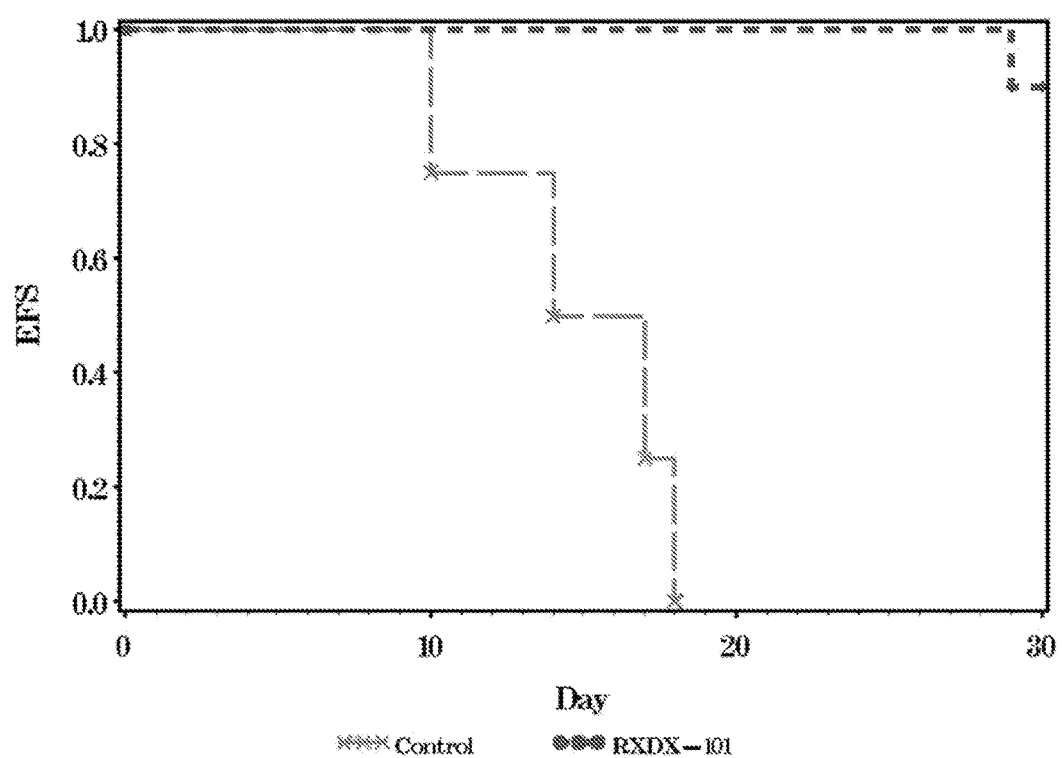

The results suggest that the tumor volume increases on average 0.1891 per day in the log of tumor volume for the control group, increases on average 0.0973 per day in the log of tumor volume for the Group 2 (treatment with N-[5-(3,5-difluorobenzyl)-1H-indazol-3-yl]-4-(4-methyl-piperazin-1-yl)-2-(tetrahydro-2H-pyran-4-ylamino) benzamide alone), and the difference in the change rate of log tumor volume between control and Group 2 is significant (p<0.0001). See FIG. 3.

The data from which the curves in FIG. 1 were derived was log transformed before fitting the model.

The estimated slopes of each trace in FIG. 1 using the linear mixed effects model were:

| | Group | | | | | |
|---|---|---|---|---|---|---|
| | Group 1 | Group 2 | Group 3 | Group 4 | Group 5 | Group 6 |
| Slope | 0.1323 | 0.0696 | 0.1192 | 0.0505 | 0.0952 | 0.0650 |

The P values for comparisons of slopes of each trace in FIG. 1 were as follows:

| Comparison | Group 1 | Group 2 | Group 3 | Group 4 | Group 5 |
|---|---|---|---|---|---|
| Group 2 | 0.0015 | | | | |
| Group 3 | | 0.0055 | | | |
| Group 4 | | 0.2527 | | | |
| Group 5 | | 0.1263 | 0.1643 | 0.0059 | |
| Group 6 | | 0.7787 | | 0.3696 | |

For example, the results suggest that the tumor volume increases on average 0.1323 per day in the log of tumor volume for Group 1 (control), and increases on average 0.0696 per day in the log of tumor volume for Group 2. The difference in the change rate of log tumor volume between Group 1 and Group 2 is significant (p=0.0015).

For the EFS traces found in FIG. 2, the p values from a log-rank test were as follows:

| Comparison | Group 1 | Group 2 | Group 3 | Group 4 | Group 5 |
|---|---|---|---|---|---|
| Group 2 | 0.0001 | | | | |
| Group 3 | 0.0206 | 0.0209 | | 0.0012 | |
| Group 4 | <0.0001 | 0.4816 | 0.0012 | | |
| Group 5 | 0.0030 | 0.0097 | 0.5344 | 0.0002 | |
| Group 6 | <0.0001 | 0.1924 | 0.0003 | 0.5753 | <0.0001 |

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present disclosure. This disclosure is susceptible to modifications in the methods and materials, as well as alterations in the fabrication methods and equipment. Such modifications will become apparent to those skilled in the art from a consideration of this disclosure or practice of the disclosure disclosed herein. Consequently, it is not intended that this disclosure be limited to the specific embodiments disclosed herein, but that it cover all modifications and alternatives coming within the true scope and spirit of the disclosure.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method for treating neuroblastoma in a patient, the method comprising administering to said patient a therapeutically effective amount of N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof, in combination with at least one topoisomerase I inhibitor and at least one alkylating agent, wherein said neuroblastoma is tropomyosin-receptor-kinase positive prior to the administration of said N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof, to said patient, and said N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof, is administered to said patient at least once per day.

2. The method according to claim 1, wherein said tropomyosin-receptor kinase is selected from TrkA, TrkB, and TrkC.

3. The method according to claim 1, wherein said tropomyosin-receptor kinase is TrkA.

4. The method according to claim 1, wherein said tropomyosin-receptor kinase is TrkB.

5. The method according to claim 1, wherein said tropomyosin-receptor kinase is TrkC.

6. The method according to claim 1, wherein said tropomyosin-receptor-kinase is at least two of TrkA, TrkB, and TrkC.

7. The method according to claim 1, wherein said topoisomerase I inhibitor is selected from irinotecan, topotecan, camptothecin and lamellarin D.

8. The method according to claim 1, wherein said alkylating agent is selected from nitrogen mustards, nitrosoureas, alkyl sulfonates, triazines, and ethylenimines.

9. The method according to claim 8, wherein said nitrogen mustards comprise mechlorethamine, chlorambucil, cyclophosphamide, ifosfamide, and melphalan.

10. The method according to claim 8, wherein said nitrosoureas comprise streptozocin, carmustine, and lomustine.

11. The method according to claim 8, wherein said alkyl sulfonates comprise busulfan.

12. The method according to claim 8, wherein said triazines comprise dacarbazine and temozolomide.

13. The method according to claim 8, wherein said ethylenimines comprise thiotepa and altretamine.

14. The method according to claim 1, wherein said N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof, is administered to said patient once per day.

15. The method according to claim 1, wherein said N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof, is administered to said patient twice per day.

16. A method for treating neuroblastoma in a patient, wherein said neuroblastoma is known to comprise one or more cells that are tropomyosin-receptor-kinase positive, comprising (a) selecting a compound which is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof, as a treatment for the patient, based on the recognition that said compound is effective in treating said neuroblastoma in said patient; and (b) administering a therapeutically effective amount of said compound with at least one topoisomerase I inhibitor and at least one alkylating agent to said neuroblastoma patient, wherein said compound is administered to said patient at least once per day.

17. The method according to claim 16, wherein said topoisomerase I inhibitor is selected from irinotecan, topotecan, camptothecin and lamellarin D.

18. The method according to claim 16, wherein said alkylating agent is selected from nitrogen mustards, nitrosoureas, alkyl sulfonates, triazines, and ethylenimines.

19. The method according to claim 16, wherein said tropomyosin-receptor kinase is selected from TrkA, TrkB, and TrkC.

20. The method according to claim 16, wherein said N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof, is administered to said patient once or twice per day.

* * * * *